United States Patent
Bae et al.

(10) Patent No.: US 7,427,445 B2
(45) Date of Patent: Sep. 23, 2008

(54) COMPOUND CAPABLE OF BEING USED IN ORGANIC LAYER OF ORGANIC LIGHT EMITTING DEVICE

(75) Inventors: Jae Soon Bae, Daejeon (KR); Min Soo Kang, Daejeon (KR)

(73) Assignee: LG Chem, Ltd., Seoul (KR)

( * ) Notice: Subject to any disclaimer, the term of this patent is extended or adjusted under 35 U.S.C. 154(b) by 565 days.

(21) Appl. No.: 10/979,819

(22) Filed: Nov. 3, 2004

(65) Prior Publication Data

US 2005/0136287 A1     Jun. 23, 2005

(30) Foreign Application Priority Data

Nov. 4, 2003  (KR) ................ 10-2003-0077707

(51) Int. Cl.
*H01L 51/54* (2006.01)
*C09K 11/06* (2006.01)
*C07D 495/08* (2006.01)
*C08G 73/06* (2006.01)

(52) U.S. Cl. .............. 428/690; 257/E51.029; 257/E51.047; 257/40; 313/504; 313/506; 428/917; 528/377; 528/380; 528/422; 528/423; 544/345

(58) Field of Classification Search .............. None
See application file for complete search history.

(56) References Cited

U.S. PATENT DOCUMENTS

| | | | | |
|---|---|---|---|---|
| 3,882,122 A | * | 5/1975 | Hagen | 544/345 |
| 3,954,794 A | * | 5/1976 | Plattier et al. | 548/359.1 |
| 6,242,561 B1 | * | 6/2001 | Mohwald et al. | 528/377 |
| 6,379,823 B1 | | 4/2002 | Nii et al. | |
| 6,413,658 B1 | | 7/2002 | Araki | |
| 7,087,283 B2 | * | 8/2006 | Wang et al. | 428/64.1 |

FOREIGN PATENT DOCUMENTS

| | | |
|---|---|---|
| JP | 10-251633 | 9/1998 |
| WO | WO 00-58418 | 10/2000 |

OTHER PUBLICATIONS

Hamada, et al. "Red Organic Light-Emitting Diodes Using An Emitting Assist Dopant" Applied Physic Letters. vol. 75, No. 12 (Sep. 1999).
International Search Report dated Feb. 23, 2005.

* cited by examiner

*Primary Examiner*—Dawn Garrett
*Assistant Examiner*—Brett A Crouse
(74) *Attorney, Agent, or Firm*—McKenna Long & Aldridge LLP

(57) ABSTRACT

Disclosed is a compound represented by the following formula 1 as a light emitting material:

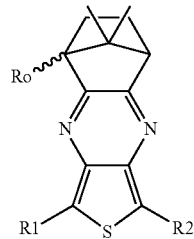

[formula 1]

wherein each of $R_0$, R1 and R2 is the same as defined herein. An organic light emitting device including a first electrode, an organic film having one or more layers and a second electrode, laminated successively, is also disclosed. At least one layer of the organic film includes at least one compound represented by formula 1. The organic light emitting device shows excellent characteristics in terms of light emitting efficiency, life time and thermal stability.

8 Claims, 2 Drawing Sheets

COMPOUND CAPABLE OF BEING USED IN ORGANIC LAYER OF ORGANIC LIGHT EMITTING DEVICE

CROSS REFERENCE TO RELATED APPLICATIONS

This application claims the benefit of Korean Patent Application No. 10-2003-77707, filed Nov. 4, 2003 in Korea, which is hereby incorporated by reference in its entirety.

TECHNICAL FIELD

The present invention relates to a novel compound for use in an organic film in an organic light emitting device and an organic light emitting device using the same.

BACKGROUND ART

In general, the so-called "organic light emitting" phenomenon (organic electroluminescence) refers to a phenomenon in which electric energy is transformed into light energy by means of an organic substance. Particularly, when an organic film is disposed between an anode and a cathode and then electric potential is applied between both electrodes, holes and electrons are injected into the organic film from the anode and the cathode, respectively. When the holes and electrons injected as described above are recombined, excitons are formed. Further, when the exitons drop to a ground state, lights are emitted.

Generally, the organic film has a multi-layer structure including different materials in each layer so as to increase the efficiency and stability of the organic light emitting device using the same film. In order to obtain high light emitting efficiency, the amounts of the holes and electrons injected from both electrodes should be similar. However, there is a great difference between the movability of holes and that of electrons in one organic substance. Therefore, it is preferable that each of the hole transport layer, light emitting layer and an electron transport layer is formed individually to permit holes and electrons to be transferred efficiently to the light emitting layer, so that density of holes and that of electrons can be balanced, thereby increasing light emitting efficiency.

Light emitting materials used in the above-described organic light emitting device can be classified into fluorescent substances derived from excited singlet states and phosphorescent substances derived from excited triplet states. Further, they can be classified into blue, green and red light emitting materials depending on light colors, and yellow and orange light emitting materials needed for realizing more natural colors. The organic substance forming a light emitting layer in a light emitting device determines the color of the light emitted from the device. Additionally, substances emitting red, green or blue light are used appropriately to realize the full spectrum of color.

Meanwhile, host/dopant systems are generally used in order to increase color purity and light emitting efficiency by means of energy transition. The principle of a host/dopant system is as follows. When a host forming a light emitting layer is mixed with a small amount of a dopant having a smaller gap between both energy zones compared to the host substance, excitons generated from the host are transported to the dopant, resulting in highly efficient light emission. During the above process, wavelength of the light emitted from the host shifts to that of the dopant. Therefore, it is possible to obtain light with a desired wavelength depending on the kind of dopant.

Among such light emitting materials, red light emitting materials intrinsically have disadvantages in that energy efficiency is low, a so-called quenching effect occurs at high concentration due to intermolecular interactions through expanded pi ($\pi$)-electrons, and that color purity decreases due to a broad light emitting range. Such disadvantages of red light emitting materials were the most serious problems inhibiting practical use of full color organic light emitting devices. Due to the above problems, red light emitting materials would rather be used as a dopant together with a host than used alone. In the former case, it is possible to improve light emitting efficiency and color purity by using an energy transition from the host substance to the red light emitting material as a dopant, as described above.

However, host/dopant-based light emitting devices tend to show degradation of color purity because light emission caused by the host may occur or the dopant may be trapped at high voltage. Such problematic phenomena result from an insufficient energy transition from the host.

Hamada et al. suggested a solution for improving light emitting efficiency and color purity in [*Applied Phys. Lett.* 75, 1682 (1999)]. More particularly, they suggested an organic light emitting device having a light emitting layer comprising at least two dopants. However, it is very difficult to deposit a host substance along with two kinds of dopant substances at the same time in a practical process for manufacturing a light emitting device. Further, when either one kind of dopant or at least two kinds of dopants are used in a light emitting layer, wavelength of the light emitted from the light emitting layer shifts to the orange zone according to the increase of current density.

Accordingly, there is a continuous demand in the art for a light emitting material providing high light emitting efficiency and color purity.

DISCLOSURE OF THE INVENTION

Figure 1:
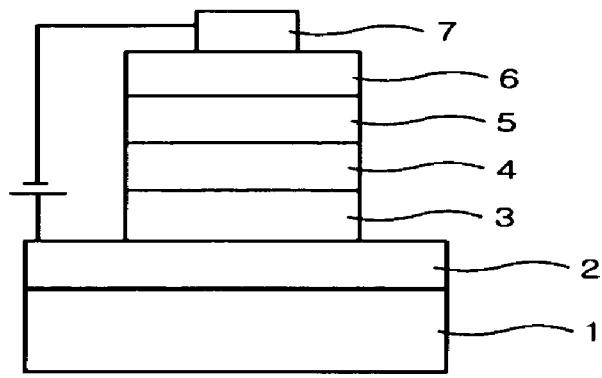
FIG. 1 shows an organic light emitting device including an organic film having four layers.

It is an object of the present invention to design a light emitting material that can solve the problems caused by intermolecular interactions. To satisfy the object, we prepared a light emitting material as an asymmetric compound such as an enantiomer by introducing a sterically bulky cycloalkyl group derived from camphorquinone into the thiophene-pyrazine molecular skeleton that is a main light emitting site; and by introducing a substituent ($R_0$) into the cycloalkyl group derived from camphorquinine to form a cycloalkyl group having a chiral carbon atom. When the light emitting material prepared as described above was incorporated into an organic film of an organic light emitting device in the form of an enantiomer or a racemate, it was possible to decrease intermolecular interactions to the highest degree. Ultimately, we have found a compound providing low quenching effect, high color purity and high light emitting efficiency, due to the decreased intermolecular interactions. Further, the compound was shown to improve the life time, efficiency and thermal stability of organic light emitting devices and to permit low-voltage drive of an organic light emitting device, when used in an organic light emitting device.

According to an aspect of the present invention, there is provided a compound represented by the following formula 1:

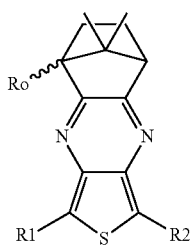

[formula 1]

wherein $R_0$ represents a lower alkyl group having 1-6 carbon atoms; and

R1 and R2 are identical or different, and each is selected from the group consisting of H; an aromatic compound and derivatives thereof; a 5-membered or 6-membered heteroaromatic compound and derivatives thereof; an aliphatic hydrocarbon having 1-20 carbon atoms and derivatives thereof; an alkylamine including an alkyl group having 1-20 carbon atoms, which is non-substituted or substituted with at least one substituent selected from the group consisting of an aliphatic hydrocarbon having 1-20 carbon atoms and derivatives thereof; an aralkylamine including an alkyl group having 1-20 carbon atoms, which is non-substituted or substituted with at least one substituent selected from the group consisting of an aliphatic hydrocarbon having 1-20 carbon atoms, an aromatic compound, a heteroaromatic compound and derivatives thereof; an arylamine non-substituted or substituted with at least one substituent selected from the group consisting of an aromatic compound, a heteroaromatic compound and derivatives thereof; and a silicon or boron compound non-substituted or substituted with at least one substituent selected from the group consisting of an aromatic compound, a heteroaromatic compound and derivatives thereof;

R1 and R2 may form a fused ring together; or

R1 and R2 are linked linearly to permit the compound represented by formula 1 to form a polymer.

According to another aspect of the present invention, there is provided an organic light emitting device comprising an organic film using the compound represented by formula 1.

Hereinafter, the present invention will be explained in detail.

The present invention provides the compound represented by formula 1.

The compound represented by formula 1 can be used as a light emitting material, particularly as a green, yellow, orange or red light emitting material and as a light emitting host or dopant in an organic light emitting device.

According to the present invention, the thiophen pyrazine skeleton in the compound of formula 1 accomplishes absorption or emission of light and determines the main wavelength of light to be emitted.

The compound according to the present invention is characterized in that the thiophen[3,4-b]pyrazine skeleton is directly linked to a cycloalkyl group through the condensation with a sterically bulky camphorquinone compound, as depicted in the above formula 1.

The cycloalkyl group introduced through the condensation with a camphorquinone compound is a relatively bulky and spherical alkyl group and thus can increase the melting point and glass transition temperature of the compound. Additionally, the cycloalkyl group can solidify the molecular structure of the compound so as to provide relatively high quantum efficiency, and can make the molecular structure so bulky that the compound is subjected to steric hindrance. Therefore, the cycloalkyl group can reduce side effects caused by intermolecular interactions, including the so-called quenching effect and decrease in color purity due to a broad light emitting range, thereby representing the characteristics of the compound itself as highly as possible. Further, introduction of the sterically bulky cycloalkyl group into the molecule of the compound of formula 1 can improve the function of the compound as a dopant capable of inhibiting intermolecular interactions in a host.

Further, the sterically bulky cycloalkyl group can serve to collect electrons on the pyrazine skeleton and thus to diversify the range of light emission by the interaction between substituents R1 and R2. The compound of formula 1 may be provided with a suitable conjugation length so as to modify the wavelength of light, or may be provided with a substituent having high electron-donating activity, such as an alkylamine group, an aralkylamine group or an arylamine group, so as to emit light. Particularly, the compound of formula 1 can provide a material that has high efficiency and is stable in the range of red light.

It is another characteristic of the present invention that the substituent ($R_0$) present on the cycloalkyl group to which the pyrazine in the thiophen[3,4-b]pyrazine skeleton is linked may provide a chiral carbon atom, thereby forming the compound of formula 1 as an asymmetric compound such as an enantiomer or as a racemate.

The present invention also includes the compounds in which $R_0$ is other substituents than a lower alkyl group having 1-6 carbon atoms, with the proviso that the compound of formula 1 can perform desired functions in an organic film of an organic light emitting device.

The compound of formula 1 can provide the effects resulting from the above-mentioned structural characteristics of formula 1, in both cases of (S)-isomer and (R)-isomer. However, when the compound of formula 1 is applied to an organic light emitting device as a racemate containing (S)-isomer and (R)-isomer in the ratio of 1:1, it is possible to obtain a light emitting efficiency increased by about 10% compared to the cases wherein each isomer is used alone. Therefore, the compound of formula 1 is preferably a mixture of (S)-isomer and (R)-isomer, such as a racemic mixture. When the compound of formula 1 is present as a racemic mixture, it is possible to reduce interactions between both enantiomeric compounds to the highest degree and thus to solve the problems of quenching effect or decrease in color purity.

Substituents R1 and R2 in the compound of formula 1 serve to modify the wavelength of light to be emitted. It is preferable that substituents R1 and R2 are substituted with a substituent increasing a conjugation length or an electron-donating or electron-withdrawing substituent.

The main skeleton of the compound of formula 1, i.e., thiophen[3,4-b]pyrazine structure is an electron-accepting portion. R1 and R2 in the 2,5-position of thiophen preferably serve as electron-donating portions so as to be balanced with the electron-accepting portion. Examples of electron-donating substituents include alkylamine groups, arylamine groups and aromatic compounds. Such substituents abundant with electrons can have a stabilized resonance structure by donating electrons to an electron-accepting portion, thereby stabilizing the whole molecular structure of the compound.

When R1 or R2 in the compound of formula 1 includes an aromatic compound, there is no particular limitation in kind of the aromatic compound because of the following reasons.

When an aromatic compound is linked with the thiophen ring on a complete plane in formula 1, a wavelength shift to a longer wavelength can be made according to the increase of conjugation bond length. However, when an aromatic compound is a sterically hindered aromatic compound that is a multicyclic compound so bulky as to twist away from the plane of the thiophen pyrazine skeleton (for example substituted or non-substituted naphthalene, anthracene, perylene, pyrene, etc.), it is difficult to make a shift to a longer wavelength. Therefore, the range of the wavelength of light to be emitted still remains in the range of red light. Accordingly, the kind of the aromatic compound included in the compound of formula 1 does not affect whether the compound could emit the light in the visible range. However, the kind of the aromatic compound has an accompanying affect on the melting point and sublimation temperature of the compound.

The above principle for the case wherein each of R1 and R2 is an aromatic compound is also applied to the cases wherein each of R1 and R2 is a derivative of aromatic compound, or an arylamine group or aralkylamine group including an aromatic compound.

Meanwhile, when the compound of formula 1 includes an alkyl group, in other words, when R1 or R2 is an alkyl group or an alkyl-substituted substituent, there is no particular limitation in length of the alkyl group. Because the length of an alkyl group included in the compound does not affect the conjugation length of the compound, it has no direct effect on the wavelength of the compound or on characteristics of a device. However, the length of an alkyl group may affect the selection of a method of applying the compound to an organic light emitting device (for example, a vacuum deposition method or a solution coating method). Therefore, there is no particular limitation in length of the alkyl group that may be included in the structure represented by formula 1.

Hereinafter, substituents R1 and R2 in the compound of formula 1 will be explained in more detail.

Examples of aromatic compounds as R1 and R2 in formula 1 include monocyclic aromatic rings such as phenyl, biphenyl and terphenyl, and multicyclic aromatic rings such as naphthyl, anthracenyl, pyrenyl and perylenyl.

Examples of heteroaromatic compounds as R1 and R2 in formula 1 include thiophene, furan, pyrrole, imidazole, thiazole, oxazole, oxadiazole, thiadiazole, triazole, pyridyl, pyridazyl, pyrazine, quinoline and isoquinoline groups.

Aliphatic hydrocarbons having 1-20 carbon atoms include both linear aliphatic hydrocarbons and branched aliphatic hydrocarbons, and particular examples thereof include alkyl groups such as methyl, ethyl, n-propyl, isopropyl, n-butyl, sec-butyl, isobutyl, t-butyl, pentyl and hexyl groups; alkenyl groups, such as styryl group, having a double bond; and alkynyl groups, such as acetylene group, having a triple bond.

The aromatic compounds, aliphatic hydrocarbons and alkyl groups that may be included in the substituted or non-substituted alkylamine groups, aralkylamine groups, arylamine groups and silicon or boron compounds are the same as defined above.

Particular examples of R1 and R2 in formula 1 include the following compounds, but are not limited thereto:

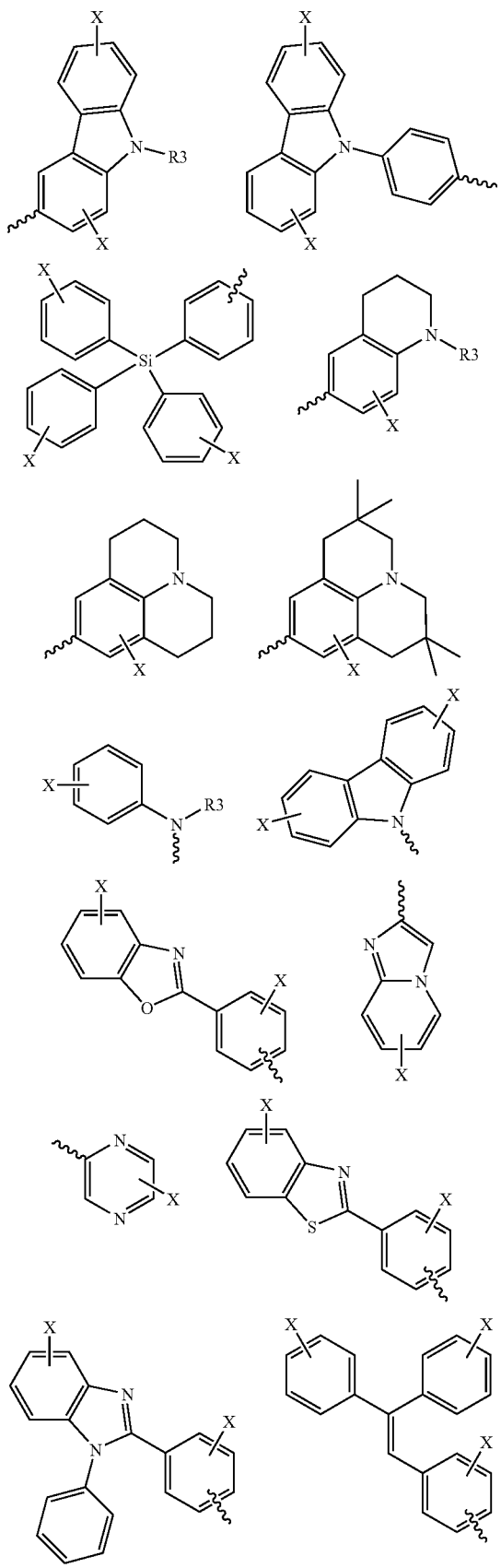

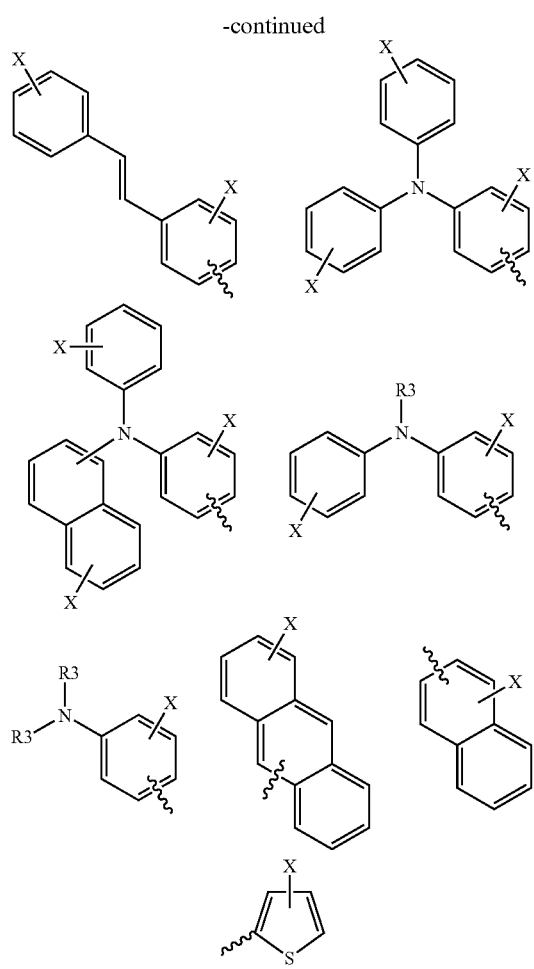

wherein

R3 is selected from the group consisting of an aromatic hydrocarbon and derivatives thereof; a 5-membered or 6-membered heteroaromatic compound and derivatives thereof; an aliphatic hydrocarbon having 1-20 carbon atoms and derivatives thereof; and a cycloalkyl group having 5-20 carbon atoms; and X is selected from the group consisting of an aromatic hydrocarbon and derivatives thereof; a 5-membered or 6-membered heteroaromatic compound and derivatives thereof; an aliphatic hydrocarbon having 1-20 carbon atoms and derivatives thereof; a cycloalkyl group having 5-20 carbon atoms; H, an arylamine group, aralkylamine group, alkylamine group, aryloxy group, nitrile group, formyl group, acetyl group, benzoyl group, amide group, ester group, styryl group, acetylene group, alkoxy group, aryloxy group, alkylthioxy group and arylthioxy group; or X may form a fused ring.

Examples of aromatic compounds as R3 and X are the same as defined above with regard to R1 and R2. Examples of heteroaromatic compounds as R3 and X are the same as defined above with regard to R1 and R2.

Examples of aliphatic hydrocarbons as R3 and X include linear or branched alkyl groups having 1-20 carbon atoms (for example, methyl, ethyl, n-propyl, isopropyl, n-butyl, isobutyl, sec-butyl, t-butyl, n-pentyl and 2-ethylhexyl). These alkyl groups may be substituted with at least one substituent selected from the group consisting of an aryl group, alkoxy group, nitro group, nitrile group, halogen atom, etc.

Particular examples of the compound of formula 1 include the compounds represented by the following formulae 1-1 to 1-41, but are not limited thereto:

[formula 1-1]

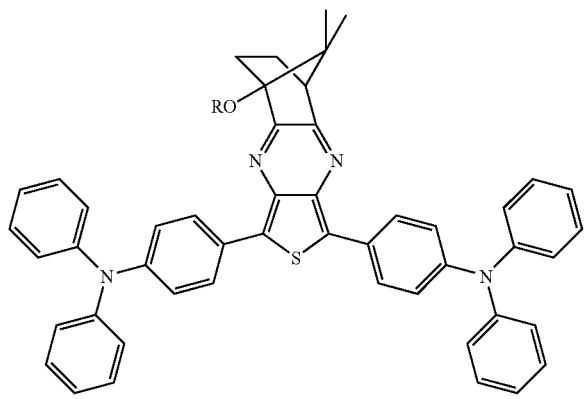

[formula 1-2]

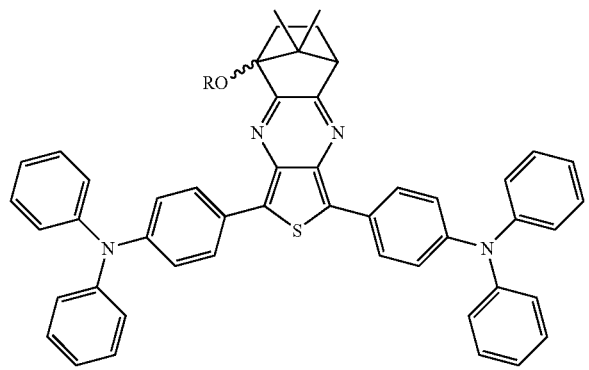

-continued
[formula 1-3]
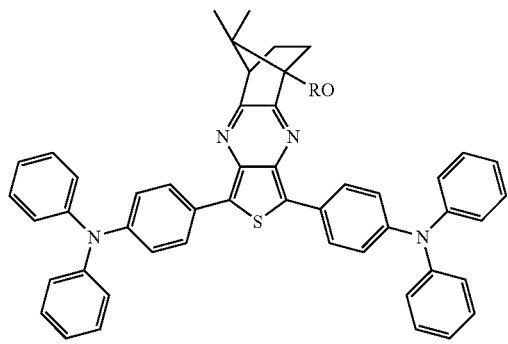
[formula 1-4]
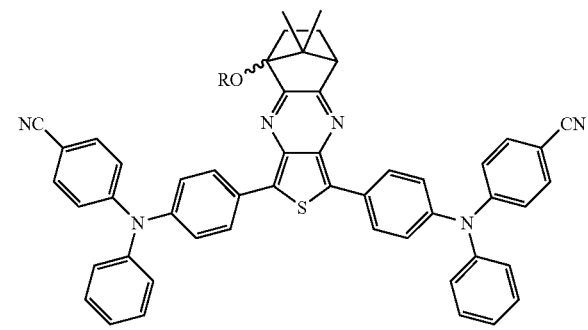
[formula 1-5]
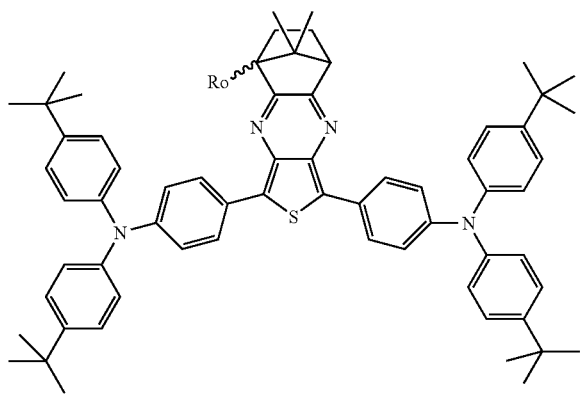
[formula 1-6]
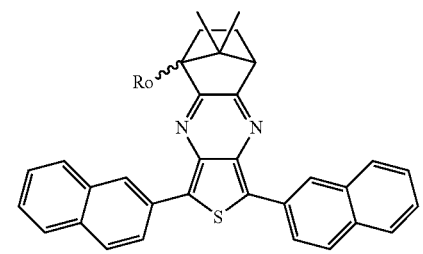
[formula 1-7]
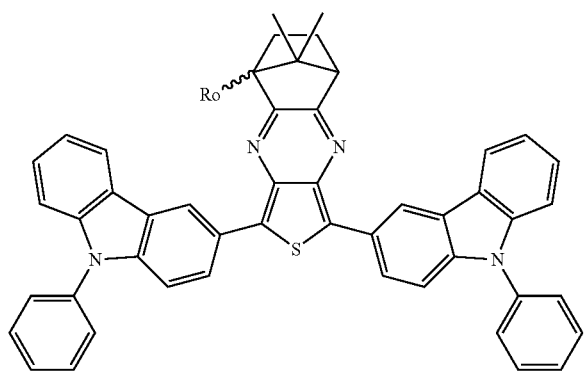
[formula 1-8]
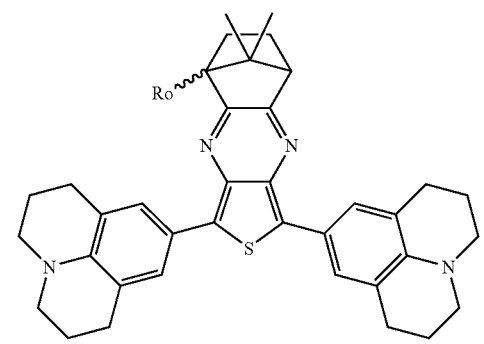
[formula 1-9]
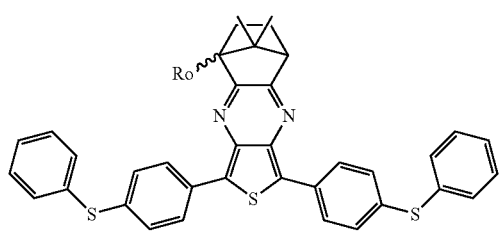
[formula 1-10]
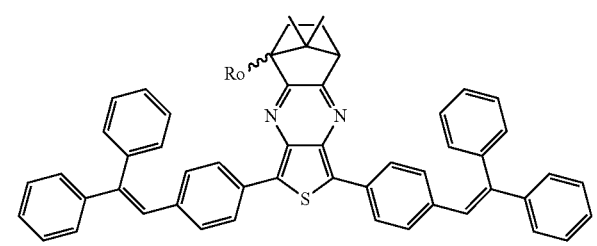

-continued
[formula 1-11]
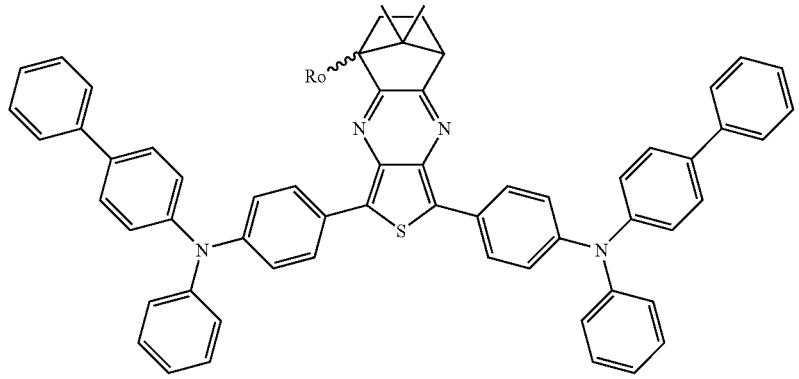
[formula 1-12]
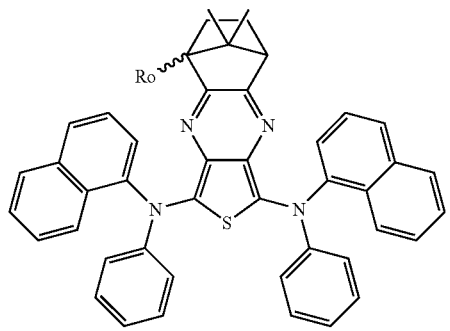
[formula 1-13]
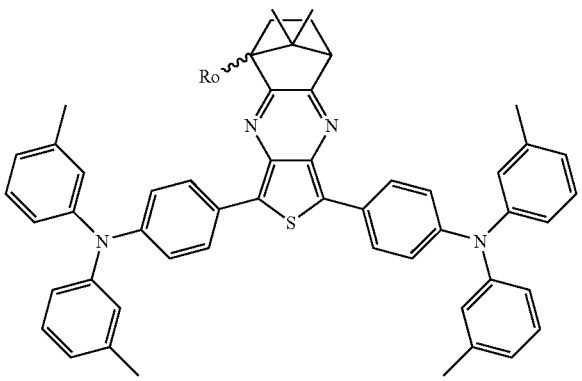
[formula 1-14]
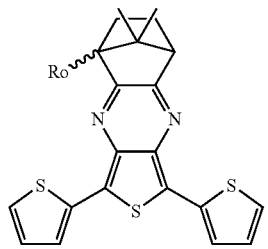
[formula 1-15]
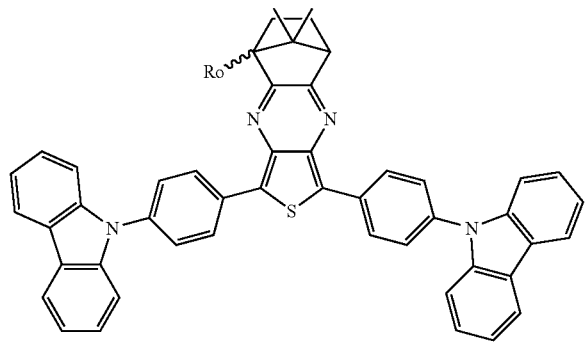
[formula 1-16]
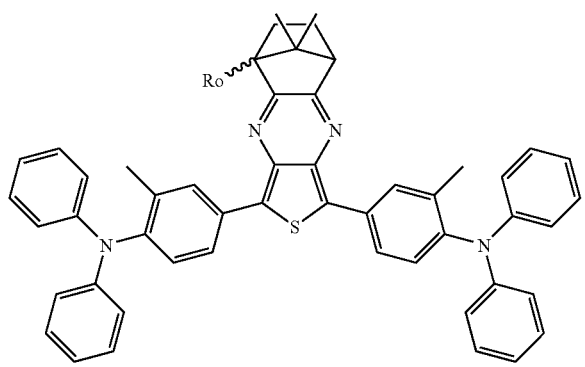
[formula 1-17]
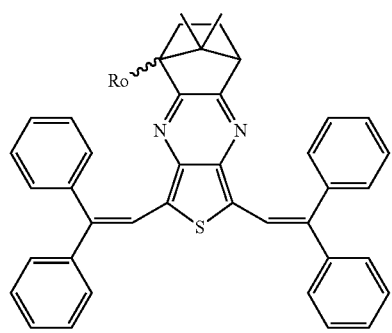

-continued
[formula 1-18]
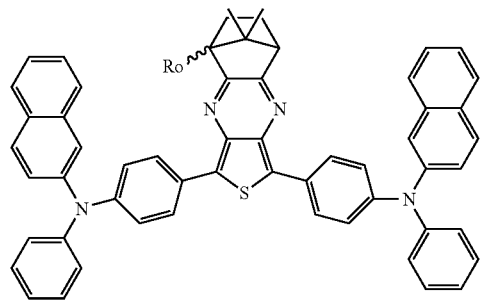
[formula 1-19]
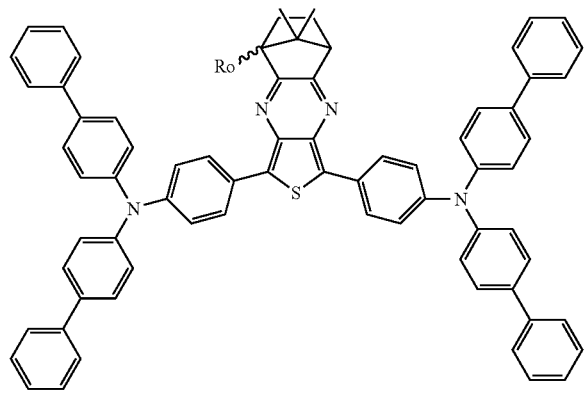
[formula 1-20]
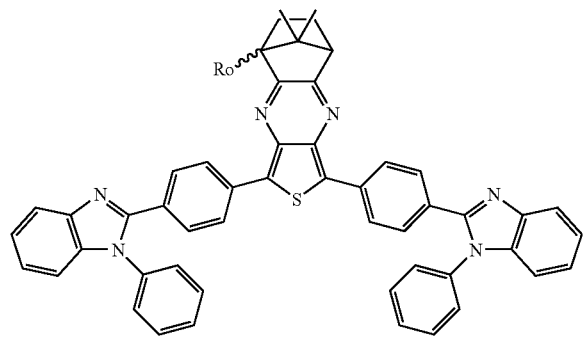
[formula 1-21]
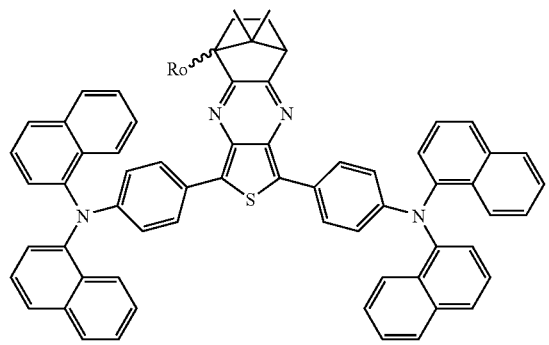
[formula 1-22]
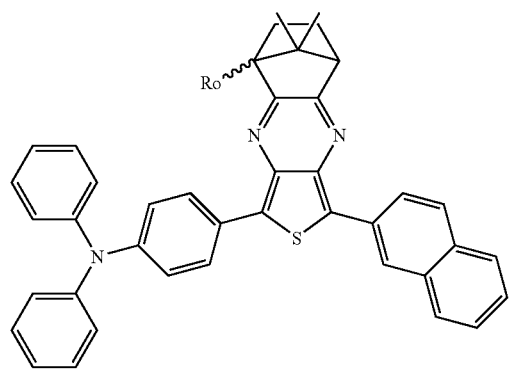
[formula 1-23]
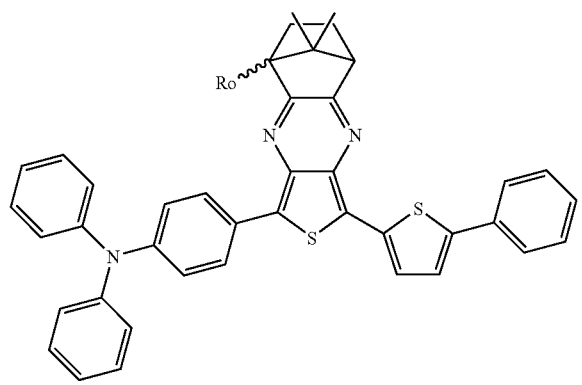
[formula 1-24]
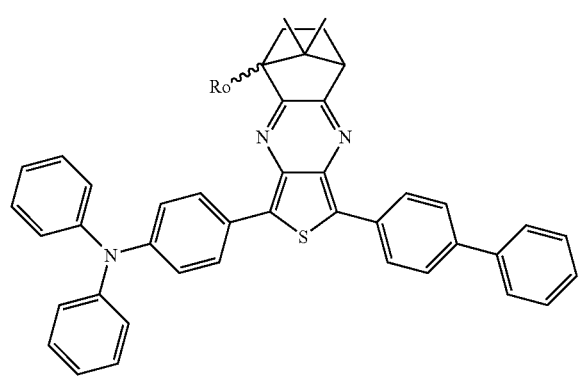
[formula 1-25]
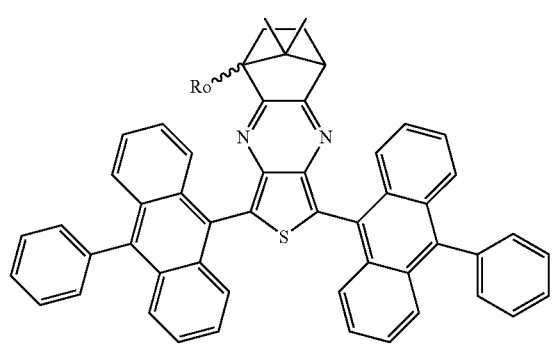

-continued
[formula 1-26]
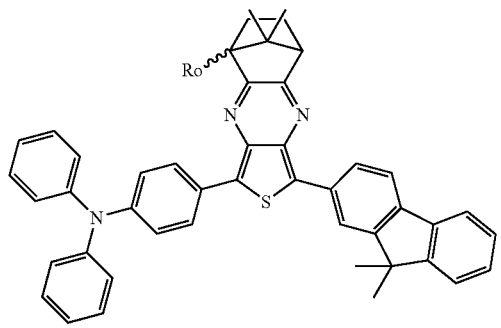
[formula 1-27]
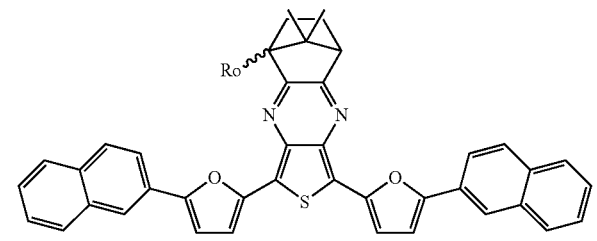
[formula 1-28]
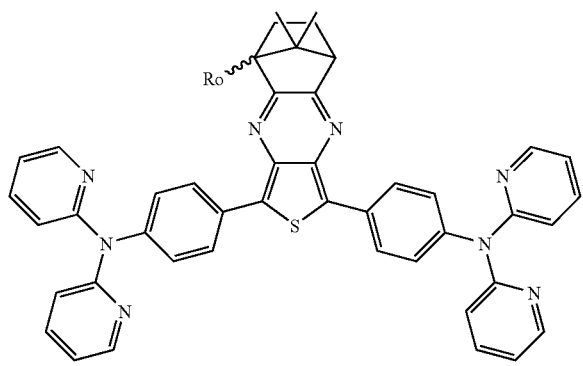
[formula 1-29]
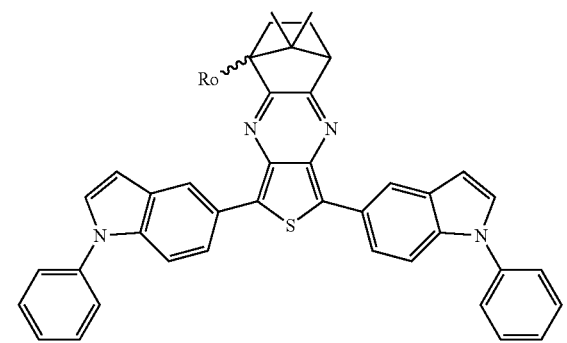
[formula 1-30]
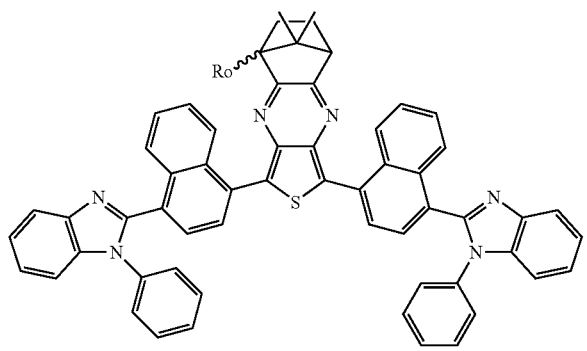
[formula 1-31]
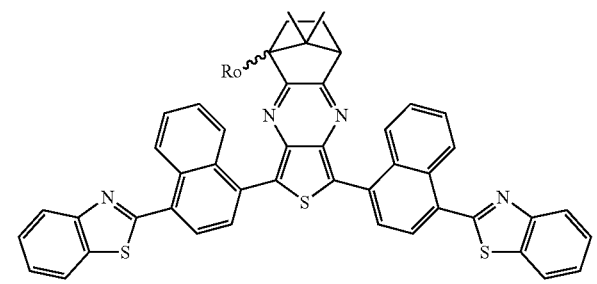
[formula 1-32]
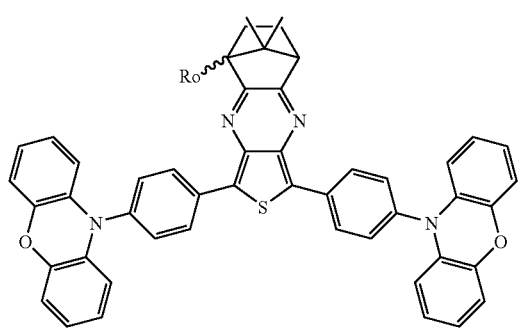
[formula 1-33]
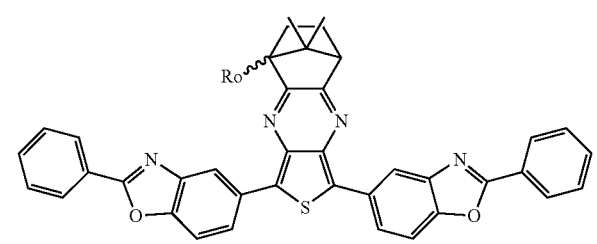

[formula 1-34]
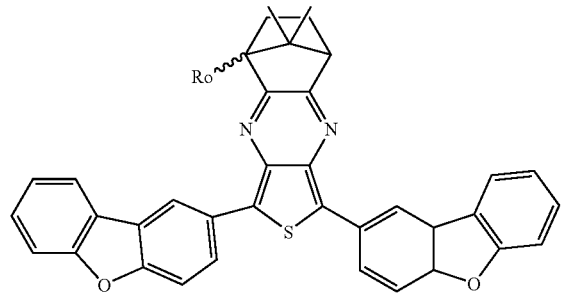
[formula 1-35]
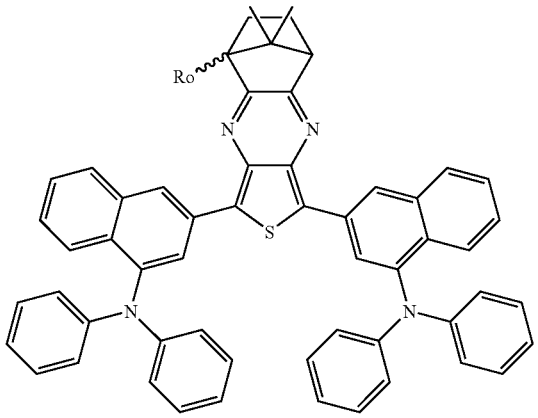
[formula 1-36]
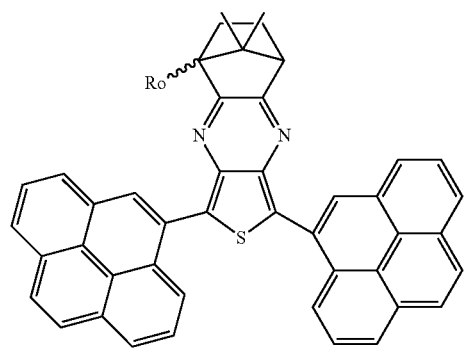
[formula 1-37]
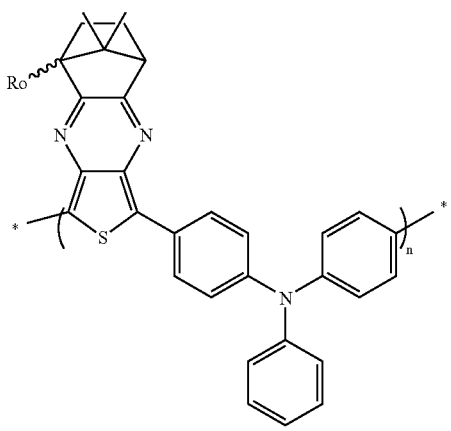
wherein n is an integer of 2 or more.
wherein n is an integer of 2 or more.
[formula 1-38]
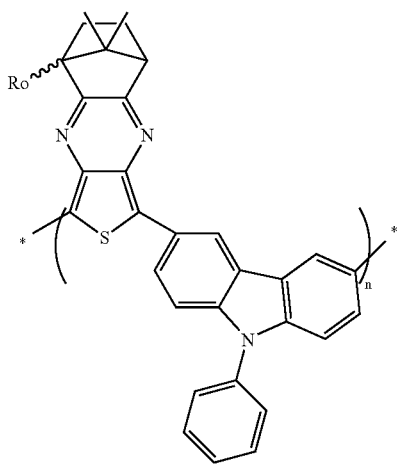
[formula 1-39]
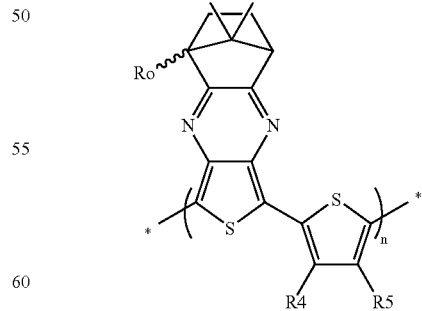
wherein n is an integer of 2 or more; and each of R4 and R5 is independently or simultaneously selected from the group consisting of H, an linear or branched aliphatic hydrocarbon having 1-20 carbon atoms, and an alkoxy group including a linear or branched aliphatic hydrocarbon having 1-20 carbon atoms; or R4 and R5 may form a fused ring together.

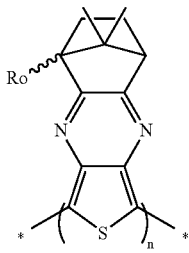

[formula 1-40]

wherein n is an integer of 2 or more.

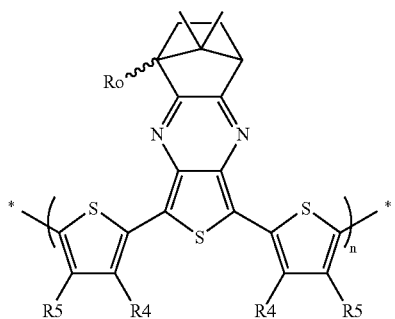

[formula 1-41]

wherein n is an integer of 2 or more; and each of R4 and R5 is independently or simultaneously selected from the group consisting of H, an linear or branched aliphatic hydrocarbon having 1-20 carbon atoms, and an alkoxy group including a linear or branched aliphatic hydrocarbon having 1-20 carbon atoms; or R4 and R5 may form a fused ring together.

Preferably, in the compounds of formula 1-37 to 1-41, the maximum value of n is 50.

The polymeric materials such as compounds of formula 1-37 and 1-38 can be used as red light emitting materials, while the thiophen polymeric materials such as compounds of formula 1-39 to 1-41 can be used also as conductive polymers, electrochromic materials, etc.

In general, the compound represented by formula 1 can be prepared by two types of methods as described hereinafter.

The first method is as follows.

Boronic acid having a substituent R1, boronic acid having a substituent R2 and 2,5-dihalogen 3,4-dinitrothiophen are coupled in an organic solvent such as dioxane, tetrahydrofuran or toluene in the presence of a base such as $K_2CO_3$ or $Na_2CO_3$ by adding a palladium (Pd) catalyst. The nitro groups ($NO_2$) in the resultant compound are reduced into amino groups ($NH_2$) by using a Fe or Sn compound. Then, the resultant compound is reacted with camphorquinone represented by the following formula 3-1, 3-2 or 3 in a solvent such as ethanol, acetic acid or a mixture thereof to form pyrazine simultaneously with dehydration (removal of water molecules). By doing so, it is possible to obtain the compound represented by formula 1.

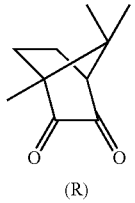

[formula 3-1]

(R)

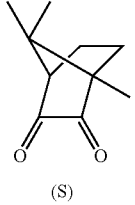

[formula 3-2]

(S)

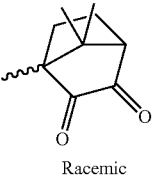

[formula 3]

Racemic

The first method may be depicted by the following reaction scheme 1.

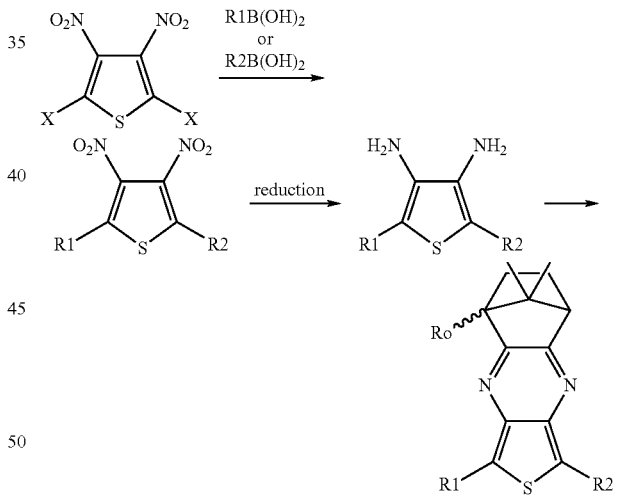

[reaction scheme 1]

wherein X is a halogen atom.

The second method is as follows.

A halogen atom (X) is introduced into the 2,5-position in 3,4-diaminothiophene by using a halogenating agent such as $Br_2$ or NBS and $Cl_2$ or NCS. The resultant 2,5-dihalogen-3,4-diaminothiophene compound is reacted with camphorquinone represented by the above formula 3-1, 3-2 or 3 in a solvent such as ethanol, acetic acid or a mixture thereof to form a thianopyrazine compound. Then, the resultant thianopyrazine compound, boronic acid having a substituent R1 and boronic acid having a substituent R2 are coupled in an organic solvent such as dioxane, tetrahydrofuran or toluene in the presence of a base such as $K_2CO_3$ or $Na_2CO_3$ by adding a palladium (Pd) catalyst. By doing so, it is possible to obtain the compound represented by formula 1. The second method may be depicted by the following reaction scheme 2.

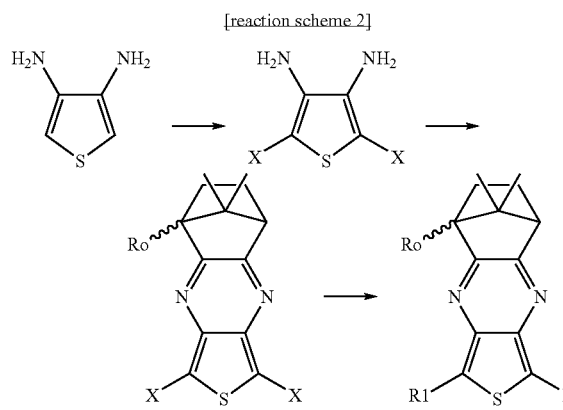

[reaction scheme 2]

wherein X is a halogen atom.

In the above methods, the halogen atom is preferably a bromine atom (Br).

Although the compounds represented by formula 1-1 to 1-36 may be prepared by using either the first method or the second method, polymeric compounds such as the compounds represented by formula 1-37 to 1-39 are preferably prepared by using the second method. Meanwhile, the polymeric compound represented by formula 1-40 may be prepared by the second method as a polymer, in the presence or absence of the step of introducing a halogen atom. Additionally, the polymeric compound represented by formula 1-41 may be prepared by using either the first method or the second method.

In a variant, each of polymeric materials of formulae 1-39, 1-40 and 1-41 may be prepared by forming a monomer first and then performing electro-polymerizaiton of the monomer.

Methods for preparing the compound represented by formula 1 will be explained in detail with reference to the following Preparation Examples.

The present invention also provides an organic light emitting device including a first electrode, an organic film having one or more layers and a second electrode, laminated successively, wherein at least one layer of the organic film contains at least one compound represented by formula 1.

The organic light emitting device according to the present invention includes a substrate, an anode, a cathode and an organic film disposed between the anode and cathode, the organic film having one or more layers. The organic film disposed between the anode and cathode may have an increased number of layers by further specializing the function of each layer. On the other hand, the organic film may have a decreased number of layers by using a multi-functional layer.

Preferably, the organic light emitting device according to the present invention have a structure including a substrate, anode, hole injection layer, hole transport layer, light emitting layer, electron transport layer and a cathode, when viewed from the bottom to the top. Additionally, a separate hole block layer may be interposed between the electron transport layer and the light emitting layer for the purpose of preventing holes from moving toward the electron transport layer.

Figure 2:
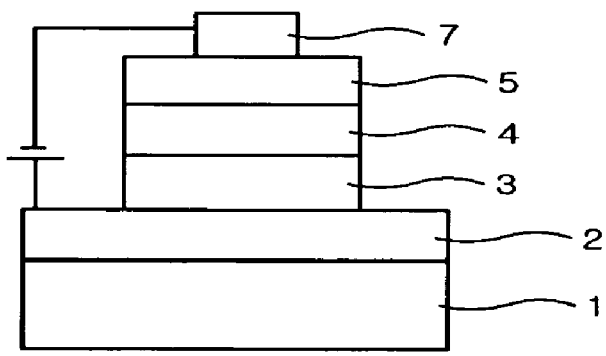
FIG. 2 shows a preferred embodiment including a light emitting layer having both functions as an electron transport layer and as a light emitting layer.
Figure 3:
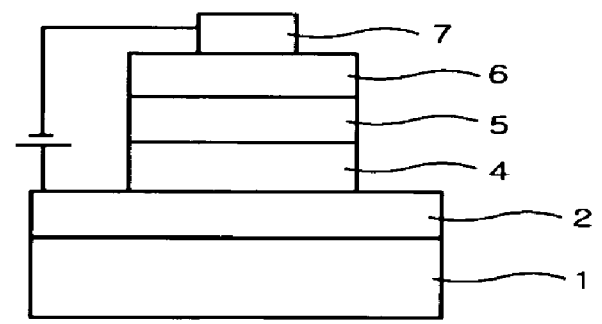
FIG. 3 shows a preferred embodiment including a hole transport layer having both functions as a hole injection layer and as a hole transport layer.
Figure 4:
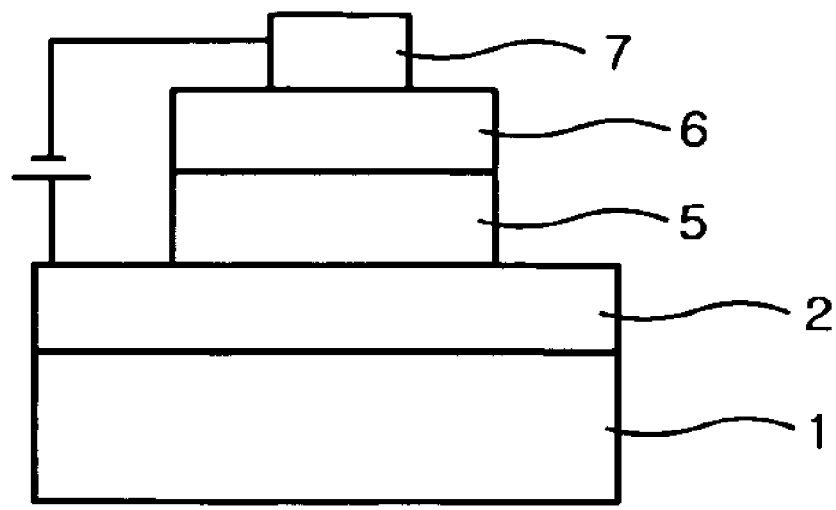
FIG. 4 shows a preferred embodiment including a light emitting layer having three functions as a hole injection layer, as a hole transport layer and as a light emitting layer as the same time.
Figure 5:
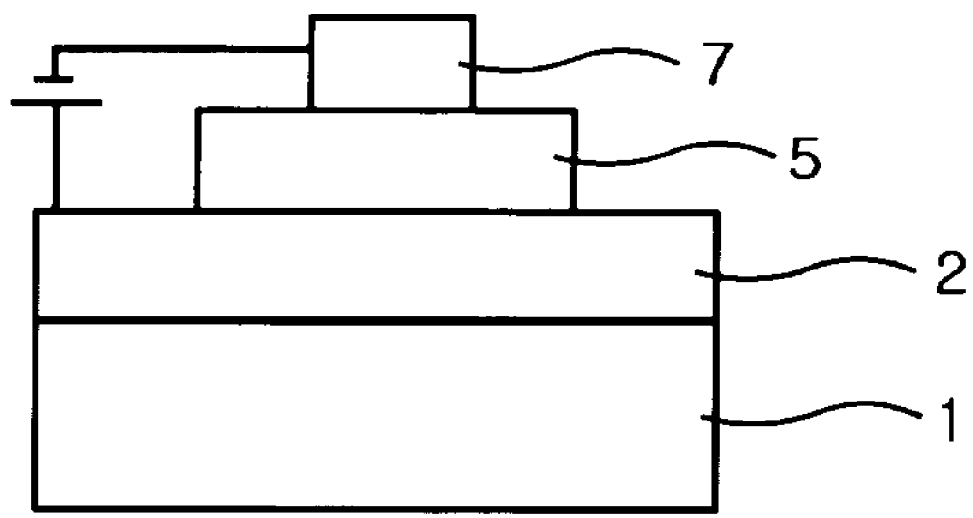
FIG. 5 shows a preferred embodiment including a light emitting layer having four functions as a hole injection layer, as a hole transport layer, an electron transport layer and a light emitting layer at the same time.

Structures of the organic light emitting device according to the present invention are exemplified in FIGS. 1 to 5, but are not limited thereto. As shown in FIG. 1, the device includes an organic film having four layers. FIG. 2 shows a preferred embodiment including a light emitting layer having both functions as an electron transport layer and as a light emitting layer. FIG. 3 shows a preferred embodiment including a hole transport layer having both functions as a hole injection layer and as a hole transport layer. FIG. 4 shows a preferred embodiment including a light emitting layer having three functions as a hole injection layer, as a hole transport layer and as a light emitting layer at the same time. Further, FIG. 5 shows a preferred embodiment including a light emitting layer having four functions as a hole injection layer, as a hole transport layer, an electron transport layer and as a light emitting layer at the same time.

In the organic light emitting device according to the present invention, each layer can be formed as a thin film, which can be prepared by a conventional method known to one skilled in the art depending on the kinds of the materials used in each layer. More particularly, the thin film may be formed by using CVD (Chemical Vapor Deposition), EB (Electron Beam Vapor Deposition), thermal vapor deposition, sputtering or high-vacuum thermal evaporation methods. Otherwise, the thin film may be formed by a solution coating method including a spin coating, roll coating, screen printing, dip coating, doctor blading, ink jet printing and thermal transfer methods.

The compound of formula 1 may be used as a light emitting material in organic light emitting devices having structures as described above. In a variant, the compound of formula 1 may be used as a light emitting host for the shift of excitation energy facilitating the light emission of other dopants, or as a dopant. Two or more of compounds represented by formula 1 may be used in combination. Further, as long as the characteristics of the present invention can be maintained, the compound of formula 1 may be used in combination with other light emitting pigments.

When the compound of formula 1 is used as a dopant having an energy gap smaller than that of the host forming a light emitting layer, excitons generated in the host are transported to the dopant, thereby permitting an increase in light emitting efficiency. Further, when the compound of formula 1 has a cycloalkyl group derived from a sterically bulky camphorquinone compound, and specially has a chiral carbon atom on the cycloalkyl group, the light emitting material of formula 1 can form a racemate capable of reducing the packing phenomenon among molecules, resulting in minimization of quenching effect.

When the compound of formula 1 is used as a dopant, it may be doped totally or partially on the layer containing the same compound. The compound of formula 1 may be doped on the layer uniformly in the direction of the thickness or may have a concentration gradient along the thickness. The amount of the compound of formula 1 to be doped preferably ranges from $10^{-3}$ to 15 wt %, and more preferably ranges from 0.1 to 10 wt %, based on the weight of the host substance.

Additionally, the compound of formula 1 can have other functions needed for an organic film of an organic light emitting device (for example, hole injection, hole transport, electron transport or electron injection) in addition to the above-described light emitting function.

Among the compounds represented by formula 1, the compound of formula 1-1 has a HOMO (Highest Occupied Molecular Orbital) level of 5.2 eV, which is similar to HOMO values of conventional materials used in a hole transport layer. Further, the compound of formula 1-1 has a work function of 4.7 eV, and thus can be used as a hole transport material. Meanwhile, when the compound of formula 1 has a longer conjugation bond or forms a polymer, it is expected that the compound has a HOMO level similar to that of poly(ethylenedioxythiophene) (PEDOT), which is a hole injection material. Meanwhile, when R1 and R2 in the compound of formula 1 are substituted with a heteroaromatic substituent (particularly, imidazole, thiazole, oxazole, pyridine, pyrazine groups, etc.), the resultant compound has a HOMO level of about 5.7 eV, which is the energy level of Alq3 as a typical example of electron transport materials. As described above, introduction of various substituents permits the compound to be transformed into a substance having n-type characteristics. When R1 and R2 are substituted with an aryl group such as phenyl or naphthyl, the resultant compound has a large energy gap corresponding to a short wavelength (for example, orange and yellow), and thus can serve also as a light emitting host.

The compound of formula 1 is preferably included in the light emitting layer in an organic light emitting device. When a hole transport layer and/or electron transport layer has an additional function as a light emitting layer without using a separately formed light emitting layer, the compound of formula 1 may be included in the hole transport layer and/or electron transport layer.

The light emitting device including the compound of formula 1 has improved life time and thermal stability. According to the introduction of a sterically bulky cycloalkyl group, (1) it is possible to increase the melting point and glass transition temperature of the compound of formula 1, resulting in improvement in thermal stability, and (2) it is possible to cause the compound of formula 1 to represent amorphous characteristics predominantly, thereby preventing the light emitting device from being damaged by crystallization caused by Joule heat generated during the operation of the organic light emitting device.

FIGS. 1 to 5 are sectional views each showing the structure of an organic light emitting device applicable to the present invention, wherein reference numeral 1 is a substrate, 2 is an anode, 3 is a hole injection layer, 4 is a hole transport layer, 5 is a light emitting layer, 6 is an electron transport layer and 7 is a cathode 107.

MODE FOR CARRYING OUT THE INVENTION

Hereinafter, the present invention will be explained in more detail through Preparation Examples, Examples, and Comparative Examples. It is to be understood that the following examples are illustrative only and the present invention is not limited thereto.

PREPARATION EXAMPLE 1

Synthesis of Compound Represented by Formula 1-1
1-1. Synthesis of the Following Compound as Intermediate

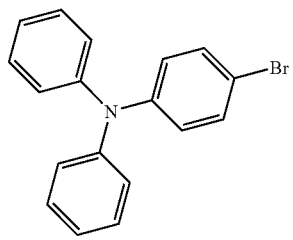

To a 500 ml flask, 17.2 g (0.1 mol) of 4-bromoaniline, 50 g (0.24 mol) of iodobenzene, 32 g (0.8 mol) of potassium hydroxide, 0.04 g (0.04 mol, 0.4 eq.) of cuprous chloride and 0.08 g (0.04 mol, 0.4 eq.) of phenanthroline were introduced and stirred for 12 hours at 180° C. under nitrogen atmosphere. The reaction mixture was cooled to room temperature and the insoluble solid salt was filtered off. The filtrate was extracted with toluene and distilled water two times and then the organic layer was collected. Toluene was removed from the organic layer under reduced pressure to provide an organic compound. The organic compound was purified by column chromatography using n-hexane as an eluent. Then, the product was precipitated with a small amount of ethanol to provide 21 g of diphenylamino 4-bromobenzene (yield 65%). m/z 324 (M+).

1-2. Synthesis of the Following Compound as Intermediate

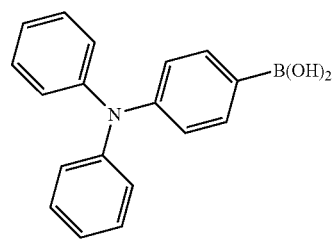

17 g (52.4 mmol) of diphenylamino 4-bromobenzene obtained from the above step 1-1 was dissolved in 200 ml of tetrahydrofuran. Next, t-butyl lithium (t-BuLi, 52 ml, 78.7 mmol, 2.5M solution in pentane) was gradually added thereto at −78° C. under nitrogen atmosphere. After 1 hour, trimethyl borate (157 mmol, 18 ml) was gradually added thereto. After 30 minutes, the cooling bath was removed and the reaction mixture was reacted for 3 hours at room temperature. After the completion of the reaction, 1N HCl (100 ml) was added and the mixture was extracted with ethyl ether. The product was dried over anhydrous magnesium sulfate, concentrated under reduced pressure and crystallized with ether. The crystallized product was filtered and dried to provide 9.8 g of diphenyl 4-aminobenzene boronic acid (yield 65%). [M+H]+ 325.

1-3. Synthesis of the Following Compound as Intermediate

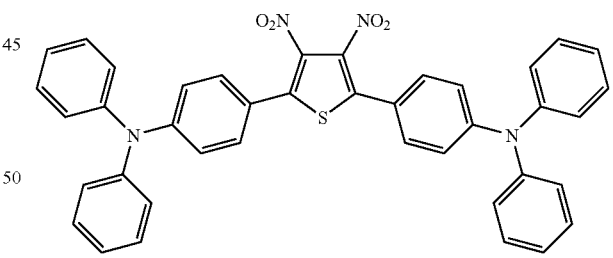

3 g (9 mmol) of 2,5-dibromo-3,4-dinitrothiophen and 8 g (27.7 mmol) of diphenyl 4-aminobenzene boronic acid obtained from the above step 1-2 were dissolved in 50 ml of tetrahydrofuran (THF). The resultant mixture, 55 ml of 2M potassium carbonate ($K_2CO_3$) and tetrakis(triphenylphosphine)palladium(0) ($Pd(PPh_3)_4$) (0.1 g, 0.09 mmol) were introduced into a 250 ml round-bottom flask and then the reaction mixture was refluxed for 24 hours. After the completion of the reaction, the reaction mixture was cooled to room temperature, and tetrahydrofuran (THF) was removed therefrom. The resultant solid was filtered after adding a small amount of ethanol, washed with water and ethanol and dried in a vacuum oven. The resultant solid was added to ethyl acetate, heated with stirring, washed to remove impurities and then dried to provide 5 g (7.6 mmol, yield 84%) of 2,5-di(triphenylamino)-3,4-dinitrothiophen. [M+H]+ 660.

1-4. Synthesis of Compound of Formula 1-1

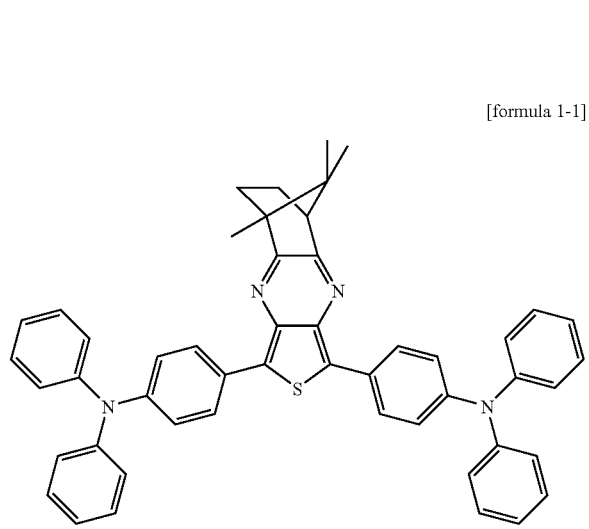

[formula 1-1]

5 g of 2,5-di(triphenylamino)-3,4-dinitrothiophen (7.6 mmol) obtained from the above step 1-3 was introduced into 40 ml of tetrahydrofuran (THF), 20 ml of EtOH and 10 ml of water. Then, 2.5 g (44.7 mmol, 6 eq.) of iron (Fe) powder was added thereto and the reaction mixture was refluxed for 48 hours. The reaction mixture was cooled to room temperature and unreacted Fe or salts thereof were filtered off. Next, the solvents were removed from the filtrate under reduced pressure. 100 ml of ethanol and 50 ml of water were added thereto and the mixture was stirred to provide a 2,5-disubstituted 3,4-diaminothiophen compound having amino groups reduced from nitro groups as a crude solid compound.

0.5 g (0.83 mmol) of the compound obtained from the above was stirred, without further purification, together with 0.14 g (0.84 mmol) of (R)-camphorquinone in 30 ml of acetone for 48 hours at 120° C. to form a solid. The resultant solid was cooled to room temperature, 30 ml of ethanol was added thereto and then the mixture was stirred to obtain a reddish purple solid. Next, the resultant solid was filtered, washed with ethanol and then dried. The product was purified by column chromatography (n-hexane/THF: 8/1) and precipitated with ethanol. The resultant product was filtered and dried to provide 0.5 g of the compound of formula 1-1 (yield 81%).

m.p.: 239.9° C.

$^1$H NMR in CDCl$_3$ δ: 8.15 (d,2H), 8.02 (d,2H), 7.29 (m,10H), 7.19 (m,12H), 7.04 (t,4H), 2.94 (d,1H), 2.25 (m,1H), 2.00 (t,1H), 1.52 (d,2H), 1.36 (s,3H), 1.11 (s,3H), 0.74 (s,3H)

Absorption Spectrum: $\lambda_{max}$ 490 nm (solvent: 2×10$^{-5}$M toluene)

Fluorescence Spectrum: $\lambda_{max}$ 641 nm (excitation wavelength 492 nm, solvent: 2×10$^{-5}$M toluene)

[M+H]+ 853.

PREPARATION EXAMPLE 2

Synthesis of Compound Represented by Formula 1-2

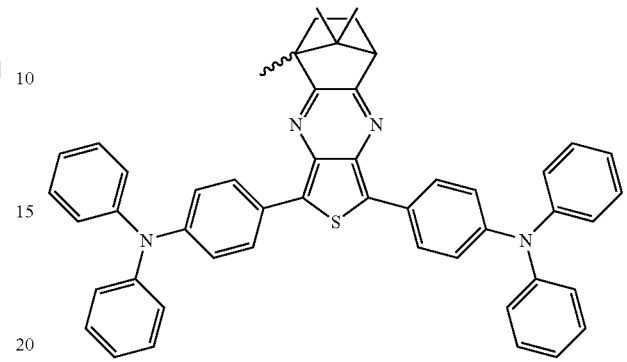

[formula 1-2]

Preparation Example 1 was repeated to provide 0.4 g (yield 67%) of the compound of formula 1-2, except that racemic camphorquinone was used instead of (R)-camphorquinone in the above step 1-4.

m.p.; 255.3° C.

$^1$H NMR in CDCl$_3$ δ: 8.15 (d,2H), 8.02 (d,2H), 7.29 (m,10H), 7.19 (m,12H), 7.04 (t,4H), 2.94 (d,1H), 2.25 (m,1H), 2.00 (t,1H), 1.52 (d,2H), 1.36 (s,3H), 1.11 (s,3H), 0.74 (s,3H)

Absorption Spectrum: $\lambda_{max}$ 490 nm (solvent: 2×10$^{-5}$M toluene)

Fluorescence Spectrum: $\lambda_{max}$ 643 nm (excitation wavelength 492 nm, solvent: 2×10$^{-5}$M toluene)

[M+H]+ 853.

PREPARATION EXAMPLE 3

Synthesis of Compound of Formula 1-5

3-1. Synthesis of the Following Compound as Intermediate

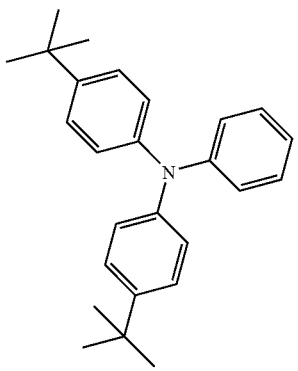

26 g (123 mmol) of 4-bromo t-butylbenzene, 4.6 g (49 mmol) of aniline, 7 g (73 mmol, 1.5 eq.) of sodium t-butoxide, 0.3 g (1 mmol) of Pd$_2$(ba)$_3$ and 0.1 g (1.5 mmol) of P(t-Bu)$_3$ were introduced to 300 ml of toluene and the reaction mixture was refluxed for 10 hours under nitrogen atmosphere. The reaction mixture was cooled to room temperature and 200 ml of distilled water was added thereto, followed by stirring. Then, the toluene phase was extracted, dried over anhydrous magnesium sulfate, filtered and was subjected to reduced pressure to remove the solvents. The reaction mixture was purified by column chromatography using n-hexane as an eluent to provide 7.4 g (20.7 mmol, yield 42%) of a white solid. [M+H]$^+$ 358.

3-2. Synthesis of the Following Compound as Intermediate

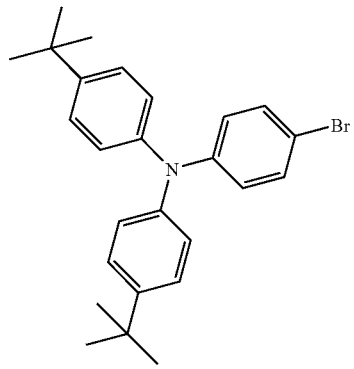

7.4 g (20.7 mmol) of the compound obtained from the above step 3-1 was introduced to 100 ml of DMF, followed by stirring. 3.7 g (20.7 mmol) of NBS was added to the reaction mixture, followed by stirring for 2 hours at 50° C. Then, 200 ml of distilled water was poured thereto, followed by stirring. The resultant solid was filtered off, dissolved in THF, and dried over anhydrous magnesium sulfate. THF used as solvent was removed under reduced pressure to obtain a liquid reaction mixture forming a solid with the lapse of time. 50 ml of ethanol was added thereto and then the resultant mixture was stirred, washed to remove impurities, filtered and dried to provide 3.2 g (7.3 mmol, yield 35%) of the target compound, N,N'-t-butyldiphenyl 4-bromoaniline. m/z 436.

3-3. Synthesis of the Following Compound as Intermediate

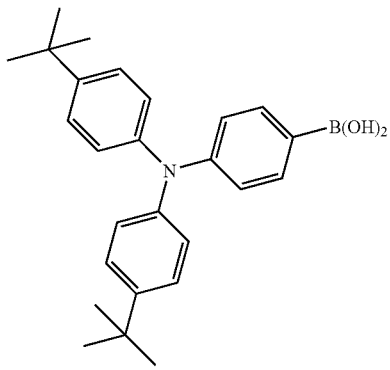

3.2 g (7.3 mmol) of the compound obtained from the above step 3-2 was dissolved in 80 ml of THF and 8 ml of t-butyl lithium (t-BuLi, 14 mmol, 2 eq. 1.7M solution in pentane) was gradually added thereto at −78° C. After 1 hour, 2.5 ml (22 mmol, 3 eq.) of trimethylborate was added thereto. After 30 minutes, the cooling bath was removed and the reaction mixture was reacted for 3 hours at room temperature. After the completion of the reaction, 50 ml of 1N HCl and 100 ml of ethyl ether were added thereto, followed by stirring for 1 hour and extraction. The resultant product was dried over anhydrous magnesium sulfate, filtered and subjected to reduced pressure to remove the organic solvents. The resultant solid was filtered, washed with petroleum ether and dried to provide 2 g (5 mmol, yield 68%) of a crude compound. [M+H]$^+$ 437.

3-4. Synthesis of the Following Compound as Intermediate

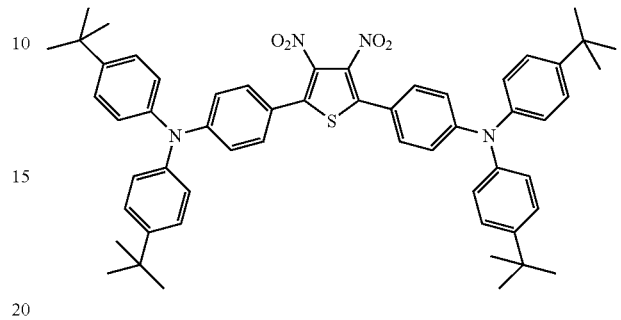

0.6 g (2 mmol) of 2,5-dibromo-3,4-dinitrothiophen dissolved in 4 ml of THF, 2 g (5 mmol) of the compound obtained from the above step 3-3, 20 ml of 2M potassium carbonate ($K_2CO_3$) and tetrakis(triphenylphosphine) palladium(0) (Pd(PPh$_3$)$_4$) (0.1 g, 0.09 mmol) were introduced into a 250 ml round-bottom flask and then the reaction mixture was refluxed for 24 hours. After the completion of the reaction, the reaction mixture was cooled to room temperature. THF was removed from the reaction mixture and a small amount of ethanol was added thereto. The resultant solid was filtered and washed with water and ethanol and dried in a vacuum oven. The resultant solid was added to ethyl acetate, heated with stirring, washed to remove impurities, filtered and then dried to provide 1.7 g (1.8 mmol, yield 90%) of the target compound. [M+H]$^+$ 885.

3-5. Synthesis of Compound of Formula 1-5

[formula 1-5]

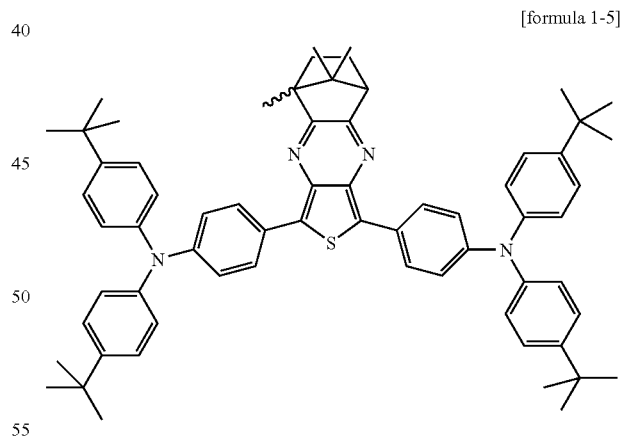

1.7 g (1.8 mmol) of the compound obtained from the above step 3-4 was introduced into 150 ml of THF, 5 ml of EtOH and 10 ml of water. Then, 0.6 g (11 mmol, 6 eq.) of iron (Fe) powder was added thereto and the reaction mixture was refluxed for 48 hours. The reaction mixture was cooled to room temperature and unreacted Fe or salts thereof were filtered off. Next, the solvents were removed from the filtrate under reduced pressure. After filtering, the product was washed with distilled water and n-hexane to provide about 1 g of the compound having amino groups reduced from nitro groups as a crude solid.

1 g of the compound obtained from the above was stirred, without further purification, together with 0.28 g (1.7 mmol) of racemic camphorquinone in 30 ml of acetic acid for 48 hours at 120° C. to form a solid. The resultant solid was cooled to room temperature, 30 ml of ethanol was added thereto and then the mixture was stirred to obtain a reddish purple solid. Next, the resultant solid was filtered, washed with ethanol and then dried. The product was purified by column chromatography (n-hexane/THF: 8/1) and precipitated with ethanol. The resultant product was filtered and dried to provide 0.5 g of the compound of formula 1-5 (yield 81%).

m.p.: 298° C.

$^1$H NMR in CDCl$_3$ δ: 8.11 (d,2H), 7.98 (d,2H), 7.28 (m,10H), 7.10 (m,12H), 2.91 (m,1H), 2.25 (m,1H), 2.00 (t,1H), 1.52 (d,2H), 1.36 (s,36H), 1.09 (s,3H), 0.72 (s,3H)

Absorption Spectrum: $\lambda_{max}$ 500 nm (solvent: 2×10$^{-5}$ M toluene)

Fluorescence Spectrum: $\lambda_{max}$ 652 nm (excitation wavelength 500 nm, solvent: 2×10$^{-5}$ M toluene)

[M+H]$^+$ 955.

PREPARATION EXAMPLE 4

Synthesis of Compound Represented by Formula 1-6
4-1. Synthesis of the Following Compound as Intermediate

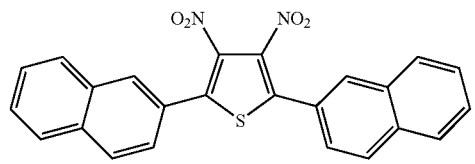

3.8 g (11.4 mmol) of 2,5-dibromo-3,4-dinitrothiophen, 5 g (29 mmol. 2.6 eq.) of naphthalene 2-boronic acid and 0.05 g (0.4 mol %) of Pd(PPh$_3$)$_4$ were refluxed in 30 ml of 2M potassium carbonate (K$_2$CO$_3$) solution and 50 ml of THF for 12 hours and then treated in the same manner as described in step 1-3 of Preparation Example 1 to provide 4.2 g (yield 86%) of the intermediate of the above formula. [M+H]$^+$ 427.

4-2. Synthesis of Compound of Formula 1-6

[formula 1-6]

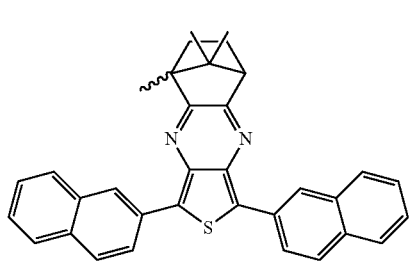

4.2 g (9.8 mmol) of the compound obtained from the above step 4-1 as intermediate and 3.2 g (58.8 mmol) of Fe powder were reacted in the same manner as described in step 1-4 of Preparation Example 1 to provide diaminothiophene.

Then, step 1-4 of Preparation Example 1 was repeated to provide 0.3 g (yield 60%) of the compound of formula 1-6, except that 0.17 g (1 mmol) of racemic camphorquinone was used instead of 0.14 g (0.84 mmol) of (R)-camphorquinone.

m.p.: 194.4° C.

$^1$H NMR in CDCl$_3$ δ: 8.8 (s,2H), 8.64 (s,2H), 8.43 (d,2H), 8.33 (d,2H), 7.97 (m,8H), 7.87 (d,4H), 7.53 (m,8H), 3.05 (d,1H), 2.25 (m,1H), 2.11 (t,1H), 1.58 (d,2H), 1.46 (s,3H), 1.16 (s,3H), 0.80 (s,3H)

Absorption Spectrum: $\lambda_{max}$ 450 nm (solvent: 2×10$^{-5}$M toluene)

Fluorescence Spectrum: $\lambda_{max}$ 584 nm (excitation wavelength nm, solvent: 2×10$^{-5}$M toluene)

[M+H]$^+$ 497.

PREPARATION EXAMPLE 5

Synthesis of Compound Represented by Formula 1-13
5-1. Synthesis of the Following Compound as Intermediate

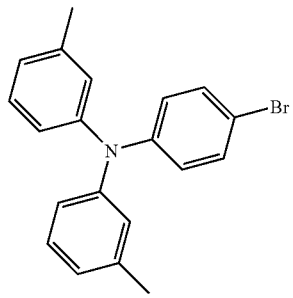

To a 500 ml flask, 7.7 g (0.45 mol) of 4-bromoaniline, 21.8 g (0.1 mol) of 3-iodotoluene, 34.4 g (0.86 mol, 8.6 eq.) of potassium hydroxide, 0.18 g (1.8 mol, 0.04 eq.) of cuprous chloride and 0.36 g (1.8 mmol, 0.04 eq.) of 1,10-phenanthroline were introduced and stirred for 12 hours at 180° C. under nitrogen atmosphere. The reaction mixture was cooled to room temperature and the insoluble solid salt was filtered off. The filtrate was extracted with toluene and distilled water two times and then the organic layer was collected. Toluene was removed from the organic layer under reduced pressure to provide an organic compound. The organic compound was purified by column chromatography using n-hexane as an eluent. Then, the product was precipitated with a small amount of ethanol to provide 8 g of 3,3'-dimethyldiphenylamino 4-bromobenzene (yield 51%). m/z 352 (M+).

5-2. Synthesis of the Following Compound as Intermediate

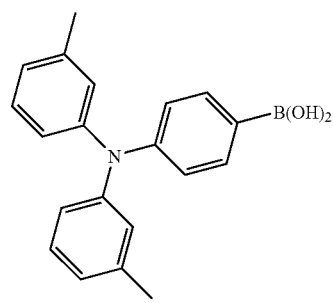

0.68 g (28 mmol, 1.4 eq.) of magnesium was introduced into a flask and then activated. Bromotriarylamine, 200 ml of THF and one drop of dibromoethane were added dropwise thereto. The reaction temperature was increased and the reaction mixture was refluxed for 4 hours. When a black solution was formed, the reaction temperature was maintained at −78° C. and trimethyl borate (59.7 mmol, 6.2 ml, 3 eq.) was gradually added thereto. After 30 minutes, the cooling bath was removed and the reaction mixture was reacted for 3 hours at room temperature. After the completion of the reaction, 1N HCl (100 ml) was added, followed by stirring for 1 hour and extraction with ethyl ether. The product was dried over anhydrous magnesium sulfate, concentrated under reduced pressure, crystallized with ether, filtered and then dried to provide 1.8 g (yield 32%) of the target compound. [M+H]$^+$ 353.

5-3. Synthesis of the Following Compound as Intermediate

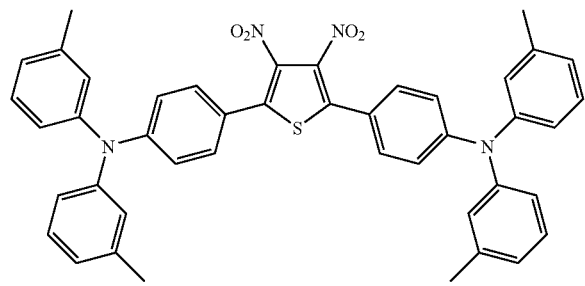

0.5 g (1.5 mmol) of 2,5-dibromo-3,4-dinitrothiophen and 1.8 g (6 mmol) of the boronic acid obtained from the above step 5-2 were dissolved in 30 ml of tetrahydrofuran (THF). The resultant mixture, 20 ml of 2M potassium carbonate ($K_2CO_3$) and tetrakis(triphenyl phosphine)palladium(0) (Pd(PPh$_3$)$_4$) (0.1 g, 0.09 mmol) were introduced into a 250 ml round-bottom flask and then the reaction mixture was refluxed for 24 hours. After the completion of the reaction, the reaction mixture was cooled to room temperature and tetrahydrofuran (THF) was removed therefrom. A small amount of ethanol was added to the resultant solid. The solid was filtered, washed with water and ethanol, and dried in a vacuum oven. The resultant solid was added to ethyl acetate, heated with stirring, washed to remove impurities, filtered and then dried to provide 0.9 g (1.2 mmol, yield 80%) of the target compound. [M+H]$^+$ 717.

5-4. Synthesis of Compound of Formula 1-13

[formula 1-13]

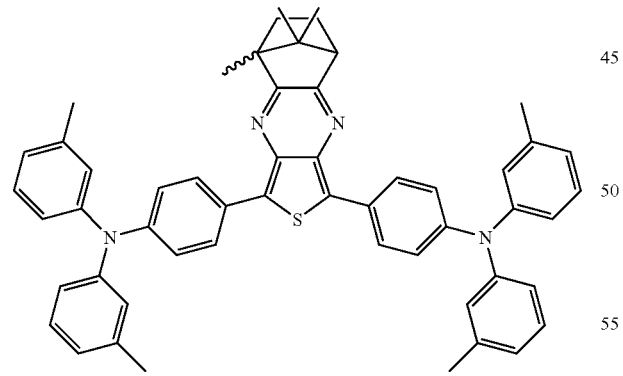

0.9 g (1.2 mmol) of the compound obtained from the above step 5-3 was introduced into 40 ml of tetrahydrofuran (THF) and 10 ml of water. Then, 0.67 g (12 mmol, 10 eq.) of iron (Fe) powder was added thereto and the reaction mixture was refluxed for 48 hours. The reaction mixture was cooled to room temperature and unreacted Fe or salts thereof were filtered off. Next, the solvents were removed from the filtrate under reduced pressure. A small amount of ethanol was added to the resultant solid. The solid was filtered, washed with water and ethanol, and dried in a vacuum oven to obtain about 0.8 g of a crude solid. 0.8 g of the compound obtained from the above and 0.24 g (1.4 mmol) of camphorquinone were refluxed in 20 ml of acetic acid for 24 hours and the reaction mixture was cooled to room temperature. 20 ml of ethanol was added thereto, and the mixture was stirred for 1 hour and then filtered. The product was purified by column chromatography (n-hexane/ethyl acetate: 8/1) and precipitated with ethanol. The resultant product was filtered and dried to provide 0.37 g of the compound of formula 1-13 (yield 40%).

m.p. 207.9° C.

$^1$H NMR in CDCl$_3$ δ: 8.13 (d,2H), 8.01 (d,2H), 7.17 (m,8H), 6.98 (m,8H), 6.87 (m,4H), 2.93 (d,1H), 2.28 (m,13H), 2.03 (q,1H), 1.52 (t,2H), 1.35 (s,3H), 1.10 (s,3H), 0.73 (s,3H)

Absorption Spectrum: $\lambda_{max}$ 499 nm (solvent: 2×10$^{-5}$M toluene)

Fluorescence Spectrum: $\lambda_{max}$ nm (excitation wavelength nm, solvent: 2×10$^{-5}$M toluene)

[M+H]$^+$ 787.

PREPARATION EXAMPLE 6

Synthesis of Compound Represented by Formula 1-14

6-1. Synthesis of the Following Compound as Intermediate

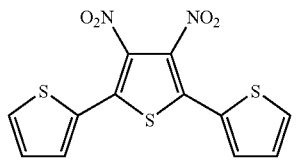

1 g (4.5 mmol) of 2,5-dibromo-3,4-dinitrothiophen, 1.73 g (13.5 mmol, 3 eq.) of thiophene 2-boronic acid and 0.05 g (1 mol %) of Pd(PPh$_3$)$_4$ (tetrakis(triphenyl phosphine)palladium(0)) were refluxed in 10 ml of 2M potassium carbonate ($K_2CO_3$) solution and 20 ml of THF for 12 hours and then treated in the same manner as described in step 1-3 of Preparation Example 1 to provide 0.4 g (yield 24.4%) of the intermediate of the above formula.

6-2. Synthesis of Compound of Formula 1-14

[formula 1-14]

The compound obtained from the above step 6-1 was reacted with Fe powder in the same manner as described in step 1-4 of Preparation Example 1 to provide diaminothiophene. Then, diaminothipohene was reacted with camphorquinone in acetic acid and the resultant product was purified by column chromatography (n-hexane/ethyl acetate: 8/1) to provide 0.2 g (yield 42%) of the compound of formula 1-14.

m.p.: Oil $^1$H NMR in CDCl$_3$ δ: 7.63 (d,2H), 7.35 (d,2H), 7.12 (t,2H), 3.00 (d,1H), 2.47 (m,1H), 2.06 (m,1H), 1.53 (d,2H), 1.42 (s,3H), 1.13 (s,3H), 0.75 (s,3H)

Absorption Spectrum: $\lambda_{max}$ 485 nm (solvent: 2×10$^{-5}$M toluene)

Fluorescence Spectrum: $\lambda_{max}$ 630 nm (excitation wavelength 481 nm, solvent: 2×10$^{-5}$M toluene)

[M+H]$^+$ 409.

PREPARATION EXAMPLE 7

Synthesis of Compound Represented by Formula 1-15

7-1. Synthesis of the Following Compound as Intermediate

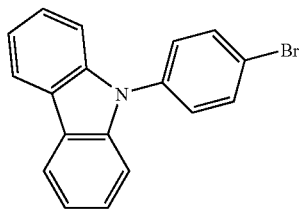

To the mixture containing 8.4 g (50 mmol) of carbazole, 16 g (57 mmol, 1.1 eq.) of 4-bromo-1-iodobenzene, 6.4 g (100 mmol, 2 eq.) of Cu, 13.8 g (100 mmol, 2 eq.) of K$_2$CO$_3$ and 0.05 g (1 mmol) of 18-crown-6, 100 ml of dichlorobenzene was added and the resultant mixture was refluxed for 16 hours under nitrogen atmosphere. The reaction mixture was cooled to room temperature, filtered to remove insoluble solid salts, and then subjected to reduced pressure to remove the organic solvents. The resultant mixture was purified by column chromatography using n-hexane as an eluent to provide 5.2 g (16.1 mmol, yield 32%) of the target compound. m/z 322 (M+).

7-2. Synthesis of the Following Compound as Intermediate

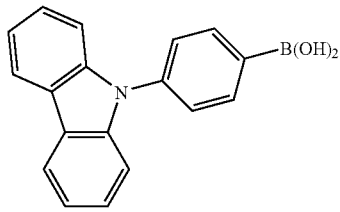

5.2 g (16.1 mmol) of the compound obtained from the above step 7-1 was dissolved in 80 ml of THF and 13.7 ml of t-butyl lithium (23.3 mmol, 1.5 eq. 1.7M solution in pentane) was gradually added thereto at −78° C. After 1 hour, 4.8 ml (46 mmol, 3 eq.) of trimethylborate was added thereto. After 30 minutes, the cooling bath was removed and the reaction mixture was reacted for 3 hours at room temperature. After the completion of the reaction, 30 ml of 1N HCl and 100 ml of ethyl ether were added thereto, followed by stirring for 1 hour and extraction. The resultant product was dried over anhydrous magnesium sulfate, filtered and subjected to reduced pressure to remove the organic solvents. The resultant solid was filtered, washed with petroleum ether and dried to provide 3.8 g (5 mmol, yield 75%) of a crude compound. [M+H]$^+$ 323.

7-3. Synthesis of the Following Compound as Intermediate

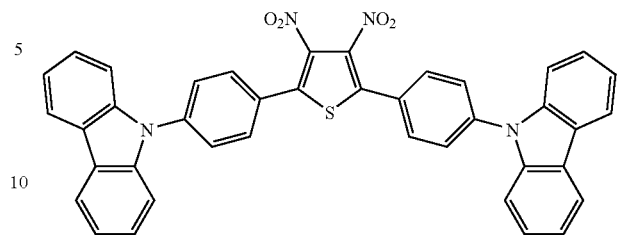

To a 100 ml round-bottom flask, 1.5 g (4.5 mmol) of 2,5-dibromo-3,4-dinitrothiophen, 3 g (10 mmol) of the compound obtained from the above step 7-2, 20 ml of 2M potassium carbonate (K$_2$CO$_3$), 30 ml of THF and tetrakis(triphenyl phosphine)palladium(0) (Pd(PPh$_3$)$_4$) (0.1 g, 0.09 mmol) were introduced. Then the reaction mixture was refluxed for 24 hours. After the completion of the reaction, the reaction mixture was cooled to room temperature. THF was removed from the reaction mixture and a small amount of ethanol was added thereto, followed by stirring to form a solid. The resultant solid was filtered and washed with water and ethanol and dried in a vacuum oven to provide 1.2 g (1.83 mmol, yield 41%) of the target compound. [M+H]$^+$ 657.

7-4. Synthesis of Compound of Formula 1-15

[formula 1-15]

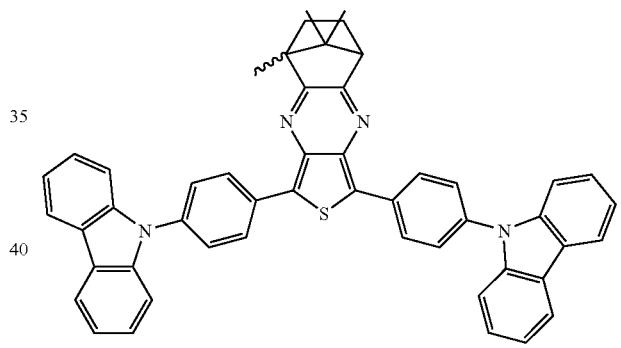

1.2 g (1.83 mmol) of the compound obtained from the above step 7-3 was introduced into 150 ml of THF, 5 ml of EtOH and 10 ml of water. Then, 0.6 g (11 mmol, 6 eq.) of iron (Fe) powder was added thereto and the reaction mixture was refluxed for 48 hours. The reaction mixture was cooled to room temperature and unreacted Fe or salts thereof were filtered off. Next, the solvents were removed from the filtrate under reduced pressure. After filtering, the product was washed with distilled water and n-hexane to provide about 1 g of a crude solid.

1 g of the crude compound, i.e., 2,5-disubstituted 3,4-diaminothiophene obtained from the above and 0.17 g (1 mmol) of camphorquinone were stirred in 20 ml of acetic acid for 48 hours at 120° C. The reaction mixture was cooled to room temperature, 20 ml of ethanol was added thereto and then the mixture was stirred to obtain a reddish purple solid. Next, the resultant solid was filtered, washed with ethanol and then dried. The product was loaded on silica gel and purified by column chromatography (n-hexane/ethyl acetate: 8/1). The product was precipitated with ethanol, and the resultant product was filtered and dried to provide 0.1 g of the compound of formula 1-15 (yield 81%).

m.p.: 336° C.

¹H NMR in CDCl₃ δ: 8.57 (d,2H), 8.47 (d,2H), 8.20 (d,4H), 7.50 (m,16H), 3.08 (d,1H), 2.32 (m,1H), 2.14 (t,1H), 1.60 (d,5H), 1.18 (s,3H), 0.83 (s,3H)

Absorption Spectrum: $\lambda_{max}$ 450 nm (solvent: $2\times10^{-5}$M toluene)

Fluorescence Spectrum: $\lambda_{max}$ 582 nm (excitation wavelength 446 nm, solvent: $2\times10^{-5}$M toluene)

[M+H]⁺ 727.

Hereinafter, the present invention will be explained in detail with reference to preferred embodiments of organic light emitting devices using the compounds obtained from the above Preparation Examples.

EXAMPLE 1

A glass substrate on which a thin film of ITO (indium tin oxide) was coated to a thickness of 1000 Å was immersed in distilled water containing a detergent to wash the substrate with ultrasonic waves. The detergent was a product commercially available from Fisher Co. The distilled water has been filtered two times by using a filter commercially available from Millipore Co. The ITO-coated substrate was washed with distilled water for 30 minutes and then further washed with ultrasonic waves two times, each for 10 minutes. After the completion of washing with distilled water, washing with ultrasonic waves was carried out by using solvents such as isopropyl alcohol, acetone and methanol, in turn. The resultant product was dried and transferred to a plasma cleaner.

Then, the substrate was cleaned for 5 minutes by using nitrogen plasma and transferred to a vacuum deposition device.

On the ITO transparent electrode prepared as described above, hexanitrile hexaazatriphenylene represented by the following formula 4 was coated to a thickness of 500 Å by thermal vacuum deposition, thereby forming a hole injection layer.

[Formula 4]

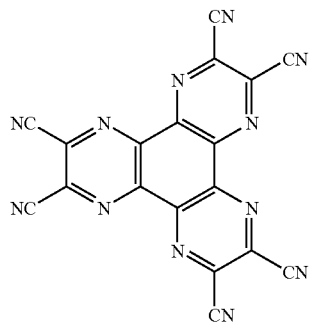

Next, NPB [N,N-bis(naphthalen-1-yl)-N,N-bis(phenyl) benzidine] of the following formula 5 as a hole transport material was coated thereon to a thickness of 400 Å by vacuum deposition, thereby forming a hole transport layer.

[formula 5]

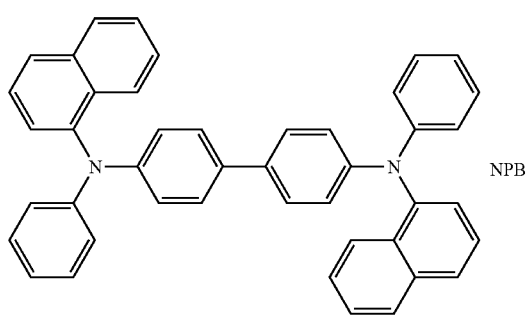

NPB

Additionally, Alq3 of the following formula 6-1 as a light emitting host was mixed with 2% of the compound of formula 1-1 obtained from Preparation Example 1 as a red dopant. Then, the mixture was coated on the hole transport layer to a thickness of 300 Å by vacuum deposition to form a light emitting layer.

[formula 6-1]

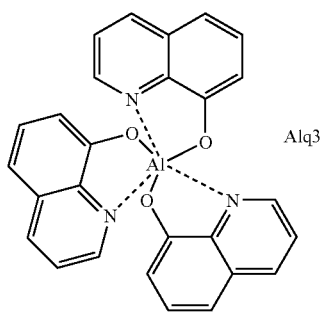

Alq3

On the light emitting layer, the compound represented by the following formula 7 capable of functioning as an electron injection/transport layer was coated to a thickness of 200 Å by vacuum deposition to complete the formation of a thin organic film.

[formula 7]

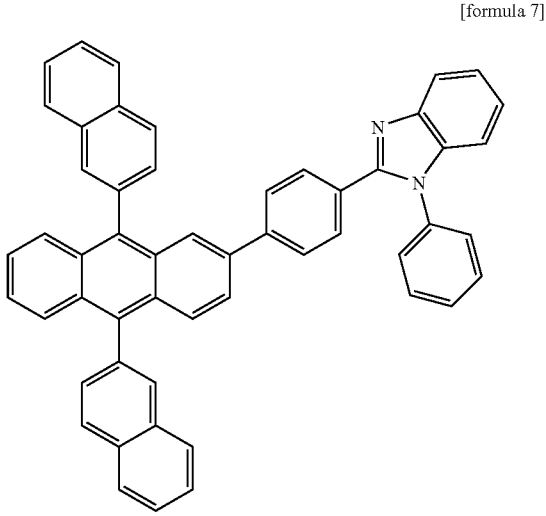

Next, on the electron injection/transport layer, lithium fluoride (LiF) and aluminum were sequentially deposited to a thickness of 12 Å and 2500 Å, respectively, to form a cathode. In the above process, deposition rate of each organic substance was maintained at 0.3 to 0.8 Å/sec and deposition rates of lithium fluoride and aluminum were maintained at 0.3 Å/sec and 1.5-2.5 Å/sec, respectively.

After a forward current of 100 mA/cm² was applied to the resultant organic light emitting device, an electric field with the driving voltage of 6.47 V was formed. Additionally, spectrum with a luminance of 2386 nit was observed with x=0.512 and y=0.449 based on the 1931 CIE color coordinate. Further, when a constant direct current was applied at a current density of 100 mA/cm², the time ($L_{0.5}$) needed for reducing the luminance to a value corresponding to 50% of the initial luminance was 420 hours.

EXAMPLE 2

Example 1 was repeated to provide an organic light emitting device, except that the compound of the following formula 6 was used as a light emitting host when forming a light emitting layer.

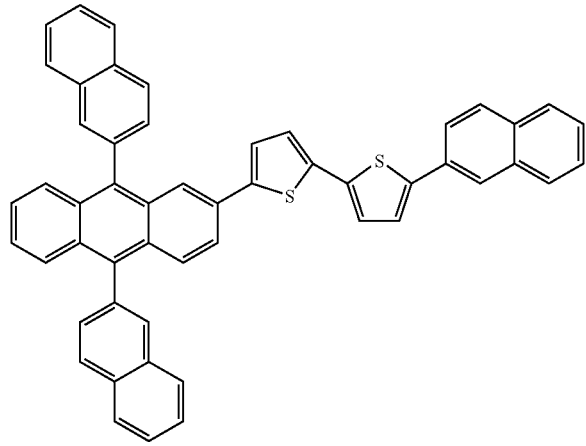

[formula 6]

After a forward current of 100 mA/cm$^2$ was applied to the resultant organic light emitting device, an electric field with the driving voltage of 5.60 V was formed. Additionally, spectrum with a luminance of 1891 nit was observed with x=0.649 and y=0.337 based on the 1931 CIE color coordinate. Further, when a constant direct current was applied at a current density of 100 mA/cm$^2$, the time ($L_{0.75}$) needed for reducing the luminance to a value corresponding to 75% of the initial luminance was 1200 hours.

EXAMPLE 3

Example 1 was repeated to provide an organic light emitting device, except that the compound of formula 1-2 obtained from Preparation Example 2 was used as a dopant when forming a light emitting layer.

After a forward current of 100 mA/cm$^2$ was applied to the resultant organic light emitting device, an electric field with the driving voltage of 7.75 V was formed. Additionally, spectrum with a luminance of 1224 nit was observed with x=0.646 and y=0.351 based on the 1931 CIE color coordinate. Further, when a constant direct current was applied at a current density of 100 mA/cm$^2$, the time ($L_{0.7}$) needed for reducing the luminance to a value corresponding to 70% of the initial luminance was 600 hours.

EXAMPLE 4

Example 1 was repeated to provide an organic light emitting device, except that the compound of the above formula 6 and the compound of formula 1-2 obtained from Preparation Example 2 was used as a light emitting host and a dopant, respectively, when forming a light emitting layer.

After a forward current of 100 mA/cm$^2$ was applied to the resultant organic light emitting device, an electric field with the driving voltage of 6.22 V was formed. Additionally, spectrum with a luminance of 1888 nit was observed with x=0.653 and y=0.345 based on the 1931 CIE color coordinate. Further, when a constant direct current was applied at a current density of 100 mA/cm$^2$, the time ($L_{0.8}$) needed for reducing the luminance to a value corresponding to 80% of the initial luminance was 600 hours.

EXAMPLE 5

Example 1 was repeated to provide an organic light emitting device, except that the compound of the above formula 6 and the compound of formula 1-5 obtained from Preparation Example 3 was used as a light emitting host and a dopant, respectively, when forming a light emitting layer.

After a forward current of 100 mA/cm$^2$ was applied to the resultant organic light emitting device, an electric field with the driving voltage of 6.38 V was formed. Additionally, spectrum with a luminance of 875 nit was observed with x=0.667 and y=0.331 based on the 1931 CIE color coordinate. Further, when a constant direct current was applied at a current density of 100 mA/cm$^2$, the time ($L_{0.95}$) needed for reducing the luminance to a value corresponding to 95% of the initial luminance was 300 hours.

EXAMPLE 6

Example 1 was repeated to provide an organic light emitting device, except that the compound of the above formula 6 and the compound of formula 1-6 obtained from Preparation Example 4 was used as a light emitting host and a dopant, respectively, when forming a light emitting layer.

After a forward current of 100 mA/cm$^2$ was applied to the resultant organic light emitting device, an electric field with the driving voltage of 5.08 V was formed. Additionally, spectrum with a luminance of 3576 nit was observed with x=0.482 and y=0.505 based on the 1931 CIE color coordinate. Further, when a constant direct current was applied at a current density of 100 mA/cm$^2$, the time ($L_{0.85}$) needed for reducing the luminance to a value corresponding to 85% of the initial luminance was 50 hours.

COMPARATIVE EXAMPLE 1

Example 1 was repeated to provide an organic light emitting device, except that DCJTB [4-(dicyanomethylene)-2-t-butyl-6-(1,1,7,7-tetramethyljulolidyl-9-enyl)-4H-pyran] represented by the following formula was used as a dopant when forming a light emitting layer.

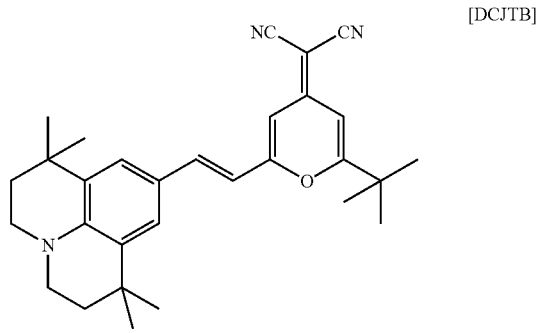

[DCJTB]

After a forward current of 100 mA/cm$^2$ was applied to the resultant organic light emitting device, an electric field with the driving voltage of 9.02 V was formed. Additionally, spectrum with a luminance of 1037 nit was observed with x=0.616 and y=0.379 based on the 1931 CIE color coordinate. Further, when a constant direct current was applied at a current density of 100 mA/cm², the time ($L_{0.5}$) needed for reducing the luminance to a value corresponding to 50% of the initial luminance was 200 hours.

COMPARATIVE EXAMPLE 2

Example 1 was repeated to provide an organic light emitting device, except that the compound of the above formula 6 and DCJTB were used as a light emitting host and a dopant, respectively, when forming a light emitting layer.

After a forward current of 100 mA/cm² was applied to the resultant organic light emitting device, an electric field with the driving voltage of 5.48 V was formed. Additionally, spectrum with a luminance of 2958 nit was observed with x=0.614 and y=0.379 based on the 1931 CIE color coordinate. Further, when a constant direct current was applied at a current density of 100 mA/cm², the time ($L_{0.5}$) needed for reducing the luminance to a value corresponding to 50% of the initial luminance was 950 hours.

COMPARATIVE EXAMPLE 3

Example 1 was repeated to provide an organic light emitting device, except that no dopant was used when forming a light emitting layer.

After a forward current of 100 mA/cm² was applied to the resultant organic light emitting device, an electric field with the driving voltage of 5.70 V was formed. Additionally, spectrum with a luminance of 3381 nit was observed with x=0.331 and y=0.561 based on the 1931 CIE color coordinate. Further, when a constant direct current was applied at a current density of 100 mA/cm², the time ($L_{0.5}$) needed for reducing the luminance to a value corresponding to 50% of the initial luminance was 400 hours.

COMPARATIVE EXAMPLE 4

Example 2 was repeated to provide an organic light emitting device, except that the compound of the above formula 6 was used as a light emitting host and no dopant was used, when forming a light emitting layer.

After a forward current of 100 mA/cm² was applied to the resultant organic light emitting device, an electric field with the driving voltage of 5.35 V was formed. Additionally, spectrum with a luminance of 4134 nit was observed with x=0.378 and y=0.580 based on the 1931 CIE color coordinate. Further, when a constant direct current was applied at a current density of 100 mA/cm², the time ($L_{0.5}$) needed for reducing the luminance to a value corresponding to 50% of the initial luminance was 750 hours.

The results obtained from the above Examples and Comparative Examples are summarized in the following Table 1.

TABLE 1

| Ex. Comp. Ex. | Host | Dopant (conc. %) | Voltage (V) | Max. Emission Wave length (nm) | External quantum efficiency (%)/ Luminance (cd/m²) @ 100 mA | Life time (hr) ($L_A$)* | Color Coordinate (x, y) |
|---|---|---|---|---|---|---|---|
| Ex. 1 | Alq3 | formula 1-1(2%) | 6.47 | 642 | 1.47/2386 | 420 ($L_{0.5}$) | (0.512, 0.449) |
| Ex. 2 | formula 6 | formula 1-1(2%) | 5.60 | 640 | 2.33/1891 | 1200 ($L_{0.75}$) | (0.638, 0.358) |
| Ex. 3 | Alq3 | formula 1-2(2%) | 7.75 | 642 | 1.08/1224 | 600 ($L_{0.7}$) | (0.646, 0.351) |
| Ex. 4 | formula 6 | formula 1-2(2%) | 6.22 | 640 | 2.46/1888 | 600 ($L_{0.8}$) | (0.653, 0.345) |
| Ex. 5 | 6 | formula 1-5(2%) | 6.38 | 650 | 1.70/875 | 300 ($L_{0.95}$) | (0.667, 0.331) |
| Ex. 6 | formula 6 | formula 1-6(2%) | 5.08 | 570 | 0.24/3576 | 50 ($L_{0.85}$) | (0.482, 0.505) |
| Comp. Ex. 1 | Alq3 | DCJTB (2%) | 9.02 | 615 | 0.94/1037 | 200 ($L_{0.5}$) | (0.616, 0.379) |
| Comp. Ex. 2 | formula 6 | DCJTB (2%) | 5.48 | 610 | 2.03/2958 | 950 ($L_{0.5}$) | (0.614, 0.379) |
| Comp. Ex. 3 | Alq3 | No | 5.70 | 535 | 1.0/3381 | 400 ($L_{0.5}$) | (0.331, 0.561) |
| Comp. Ex. 4 | formula 6 | No | 5.35 | 540 | 1.21/4134 | 750 ($L_{0.5}$) | (0.378/0.580) |

($L_A$)* means the life time during which the luminance reduces to A × 100% of the initial luminance.

As shown in Table 1, when the compound of formula 1 is used in an organic light emitting device, it is possible to obtain excellent red color purity, to cause the device to be driven at low voltage, and to improve the life time of the device.

Example 6 using the compound of formula 1-6 as a dopant shows a lower efficiency compared to other Examples using the compound according to the present invention. However, it is considered that a preferred organic light emitting device can be provided according to Example 6 by using a suitable host.

COMPARATIVE EXAMPLE 5

Example 1 was repeated to provide an organic light emitting device, except that a compound similar to the compound of formula 1-1 (with the exception that the compound was substituted with dimethyl group instead of cycloalkyl group) was used as a dopant, when forming a light emitting layer.

In the compound used in this example, a stacking phenomenon occurred among flat-like molecules resulting in intermolecular interactions, and thus the light emitting efficiency decreased. In fact, when doped to Alq3 at a concentration of 2%, the compound of formula 1-1 and the dimethyl-substituted compound showed quantum efficiency/luminance (cd/m²) results of 1.08/1224 (cd/m²) and 0.19/61 (cd/m²), respectively, at a current density of 100 mA/m².

INDUSTRIAL APPLICABILITY

As can be seen from the foregoing, the compound of formula 1 according to the present invention can provide a highly efficient light emitting material that is capable of emitting yellow, orange or red light and has excellent thermal stability. Further, when the compound of formula 1 is used as a light emitting host or dopant in an organic light emitting device, it is possible to improve the life time of the device and to cause the device to be driven at low voltage.

While this invention has been described in connection with what is presently considered to be the most practical and preferred embodiment, it is to be understood that the invention is not limited to the disclosed embodiment and the drawings. On the contrary, it is intended to cover various modifications and variations within the spirit and scope of the appended claims.

The invention claimed is:

1. A compound represented by formula 1:

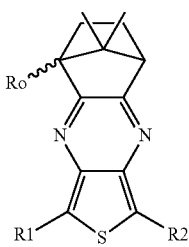

[formula 1]

wherein $R_0$ represents a lower alkyl group having 1-6 carbon atoms; and

R1 and R2 are identical or different, and each is selected from the group consisting of H; an aromatic compound and derivatives thereof; a 5-membered or 6-membered heteroaromatic compound and derivatives thereof; an aliphatic hydrocarbon having 1-20 carbon atoms and derivatives thereof an alkylamine including an alkyl group having 1-20 carbon atoms, which is non-substituted or substituted with at least one substituent selected from the group consisting of an aliphatic hydrocarbon having 1-20 carbon atoms and derivatives thereof; an aralkylamine including an alkyl group having 1-20 carbon atoms, which is non-substituted or substituted with at least one substituent selected from the group consisting of an aliphatic hydrocarbon having 1-20 carbon atoms, an aromatic compound, a heteroaromatic compound and derivatives thereof; an arylamine non-substituted or substituted with at least one substituent selected from the group consisting of an aromatic compound, a heteroaromatic compound and derivatives thereof; and a silicon or boron compound non-substituted or substituted with at least one substituent selected from the group consisting of an aromatic compound, a heteroaromatic compound and derivatives thereof;

R1 and R2 may form a fused ring together; or

R1 and R2 are linked linearly to permit the compound represented by formula 1 to form a polymer.

2. The compound according to claim 1, wherein the compound is selected from the group consisting of compounds represented by formulae 1-1 to 1-41:

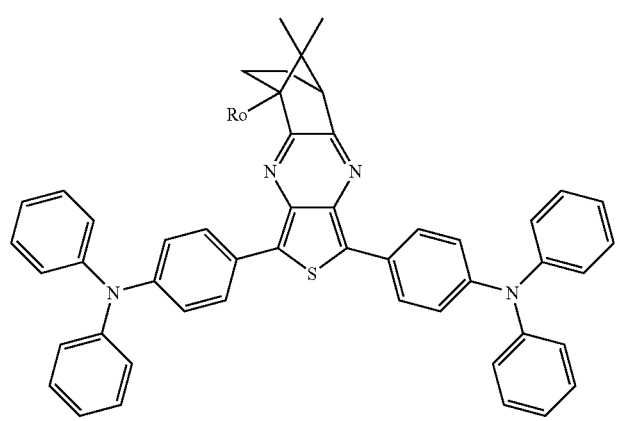

[formula 1-1]

-continued
[formula 1-2]
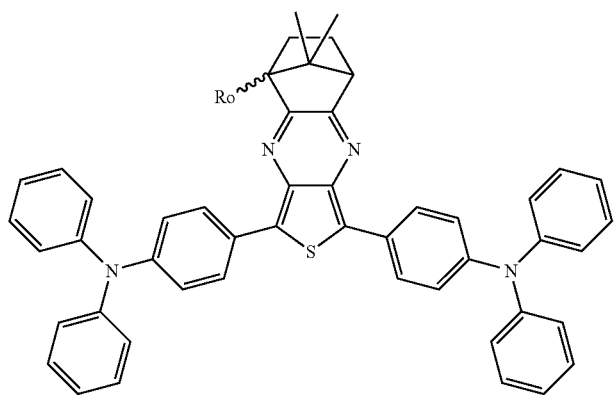
[formula 1-3]
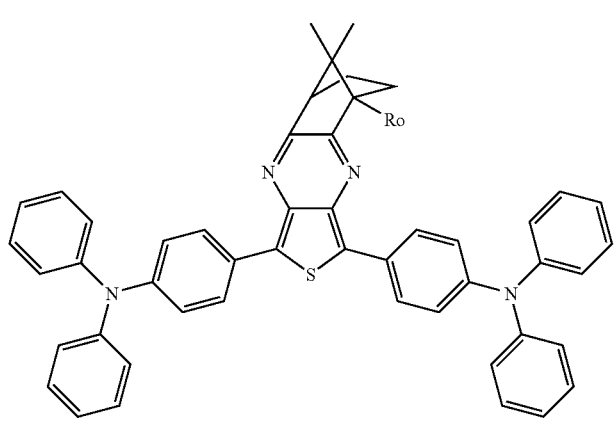
[formula 1-4]
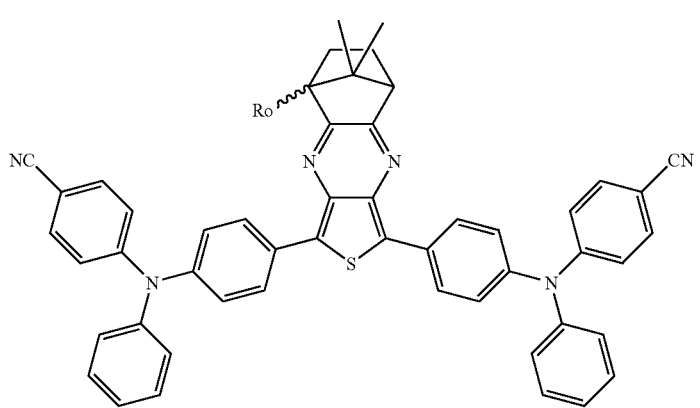

-continued
[formula 1-5]
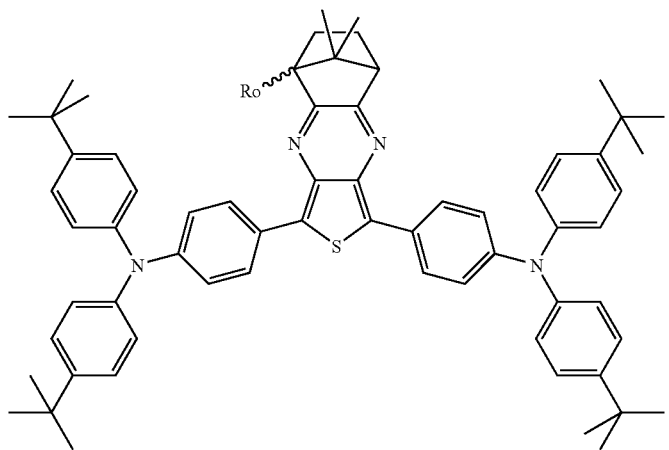
[formula 1-6]
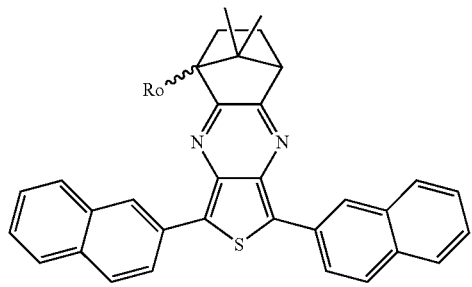
[formula 1-7]
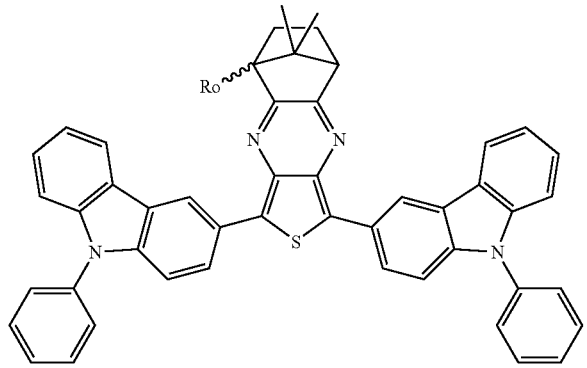
[formula 1-8]
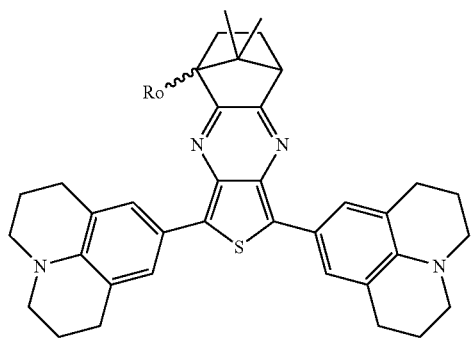

[formula 1-9]
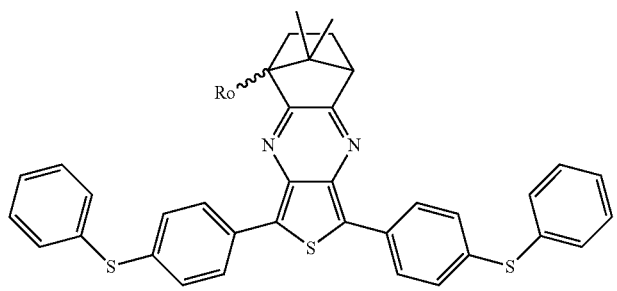
[formula 1-10]
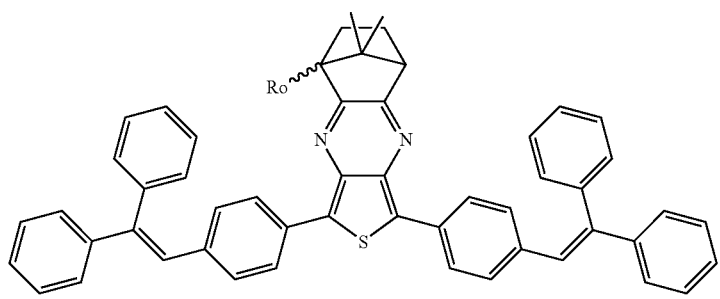
[formula 1-11]
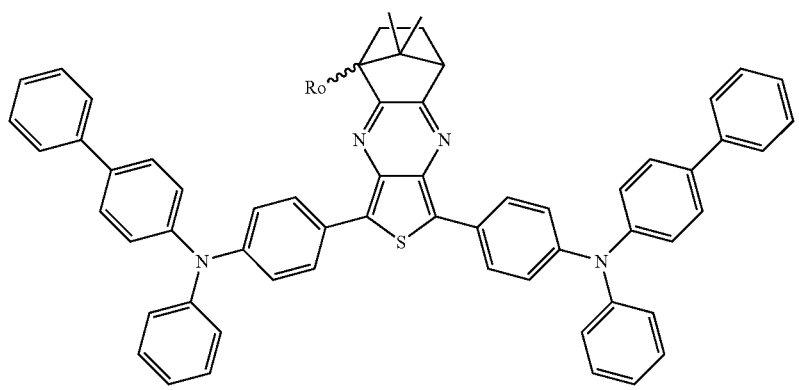
[formula 1-12]
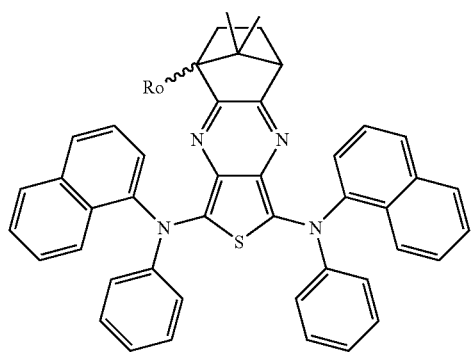

[formula 1-13]
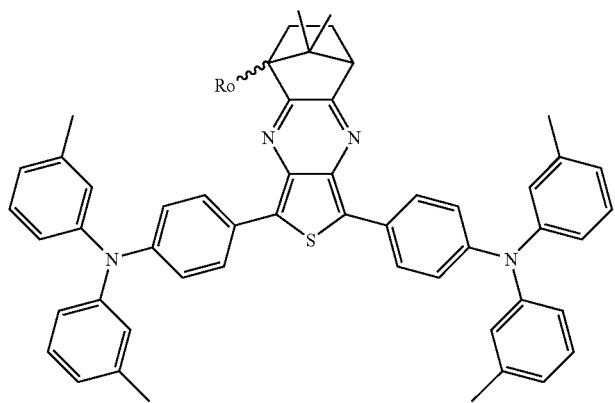
[formula 1-14]
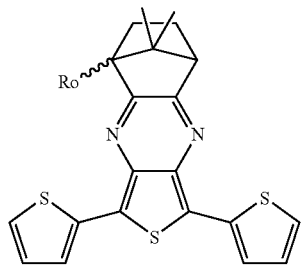
[formula 1-15]
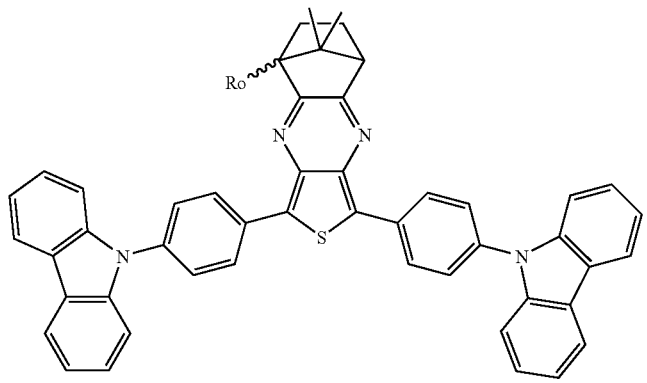
[formula 1-16]
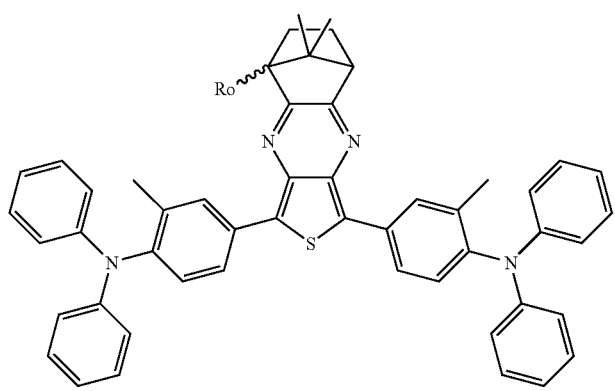

-continued
[formula 1-17]
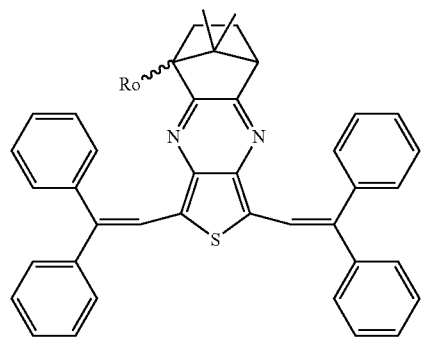
[formula 1-18]
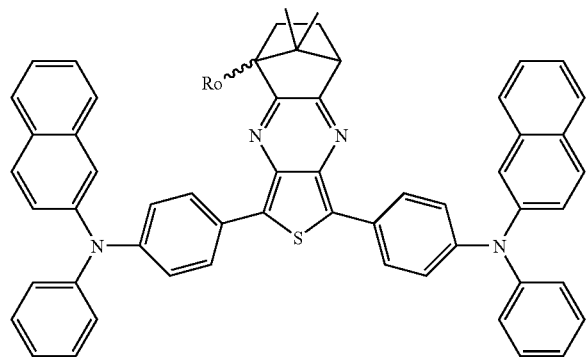
[formula 1-19]
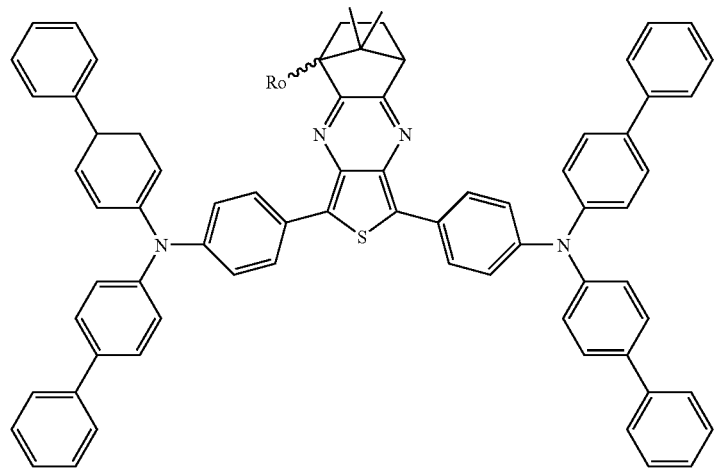
[formula 1-20]
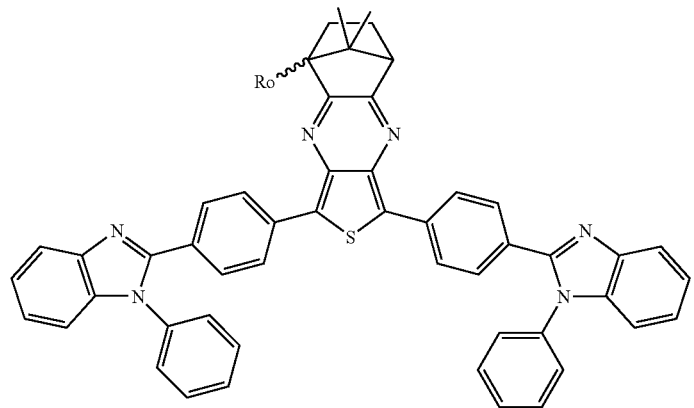

[formula 1-21]
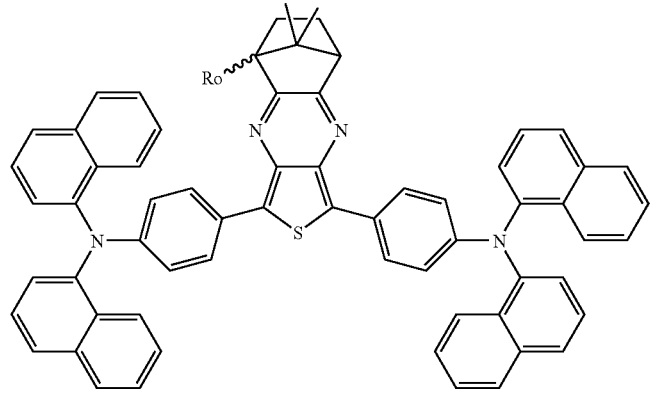
[formula 1-22]
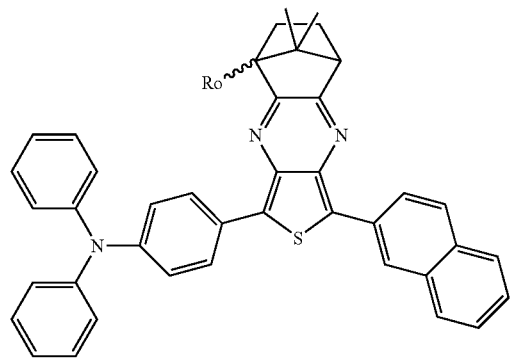
[formula 1-23]
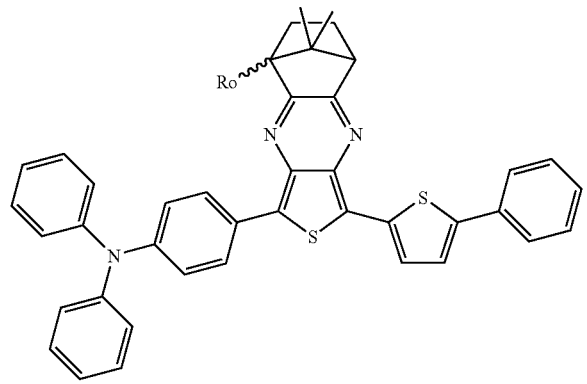
[formula 1-24]
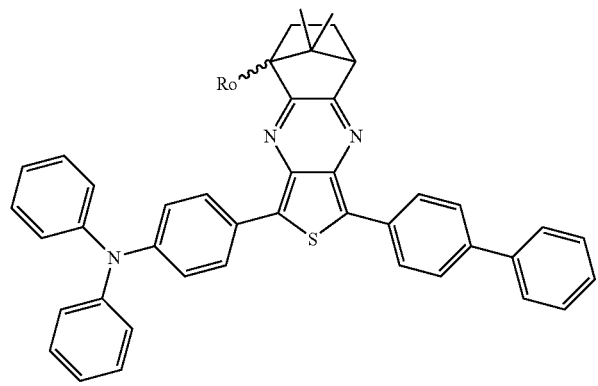

-continued
[formula 1-25]
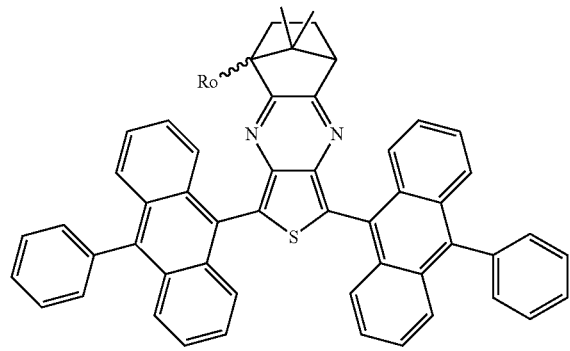
[formula 1-26]
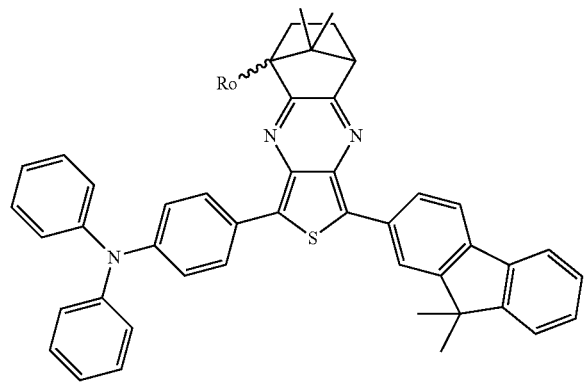
[formula 1-27]
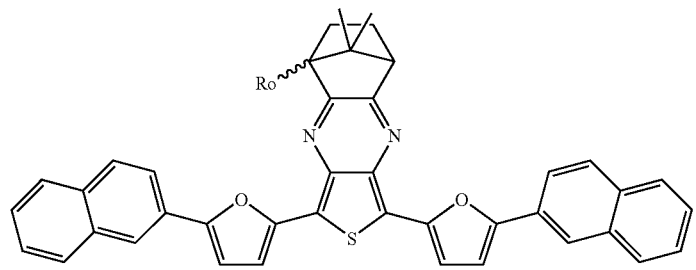
[formula 1-28]
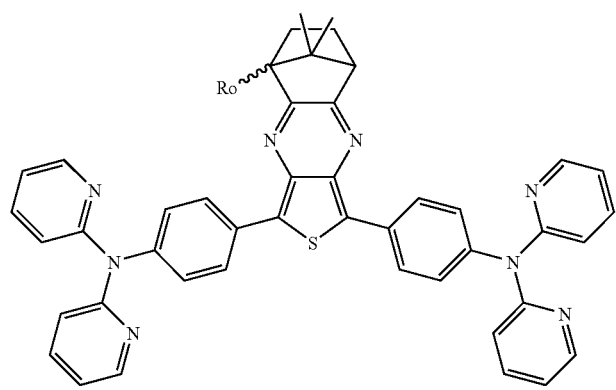

[formula 1-29]
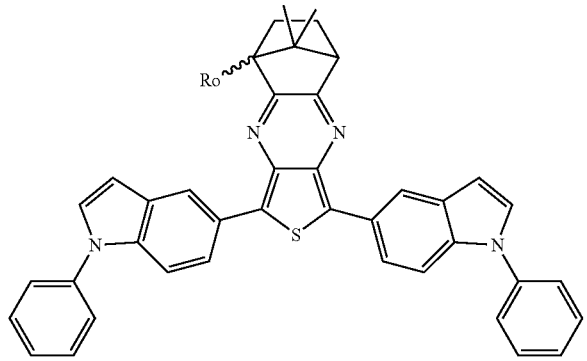
[formula 1-30]
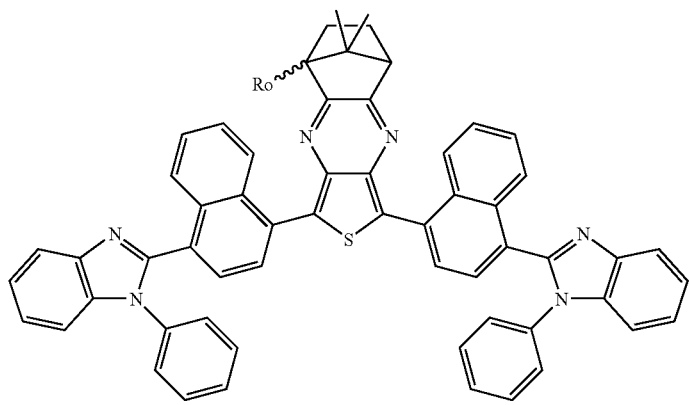
[formual 1-31]
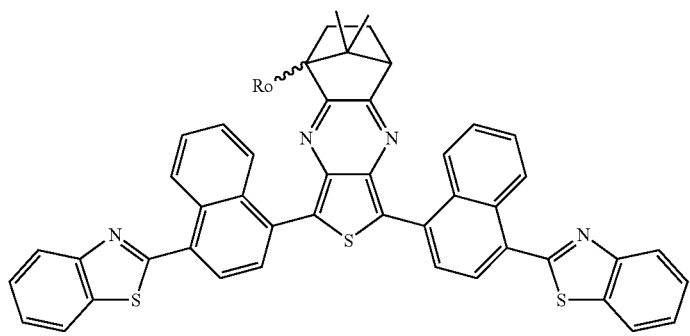
[formula 1-32]
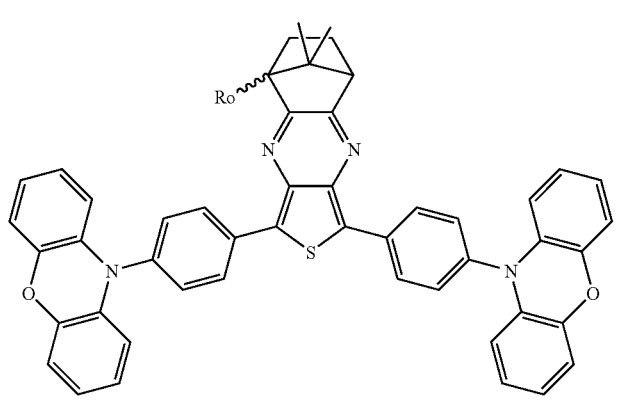

[formula 1-33]
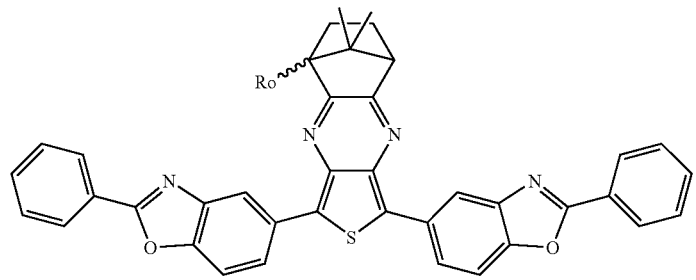
[formula 1-34]
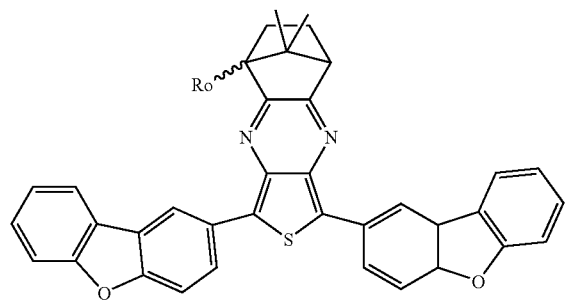
[formula 1-35]
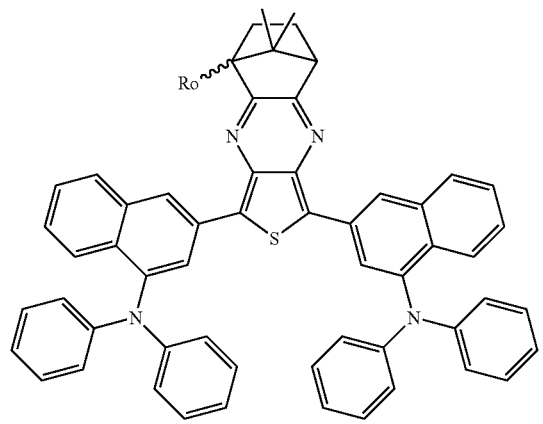
[formula 1-36]
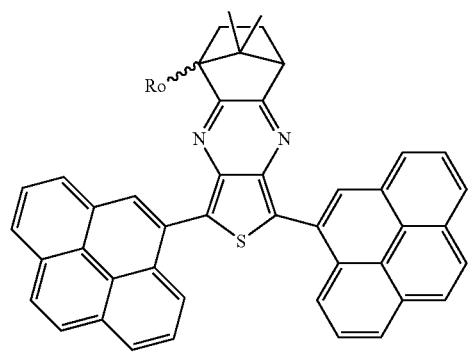

-continued
[formula 1-37]
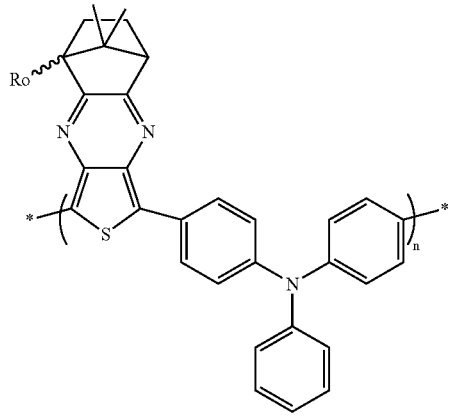
wherein n is an integer of 2 or more;
[formula 1-38]
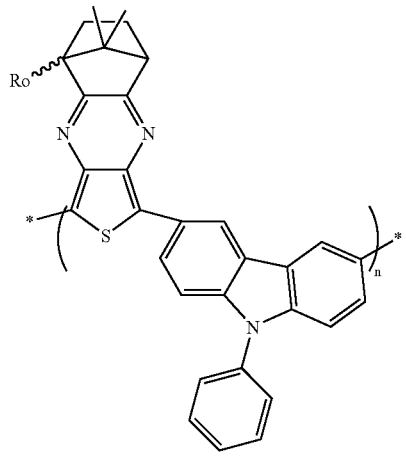
wherein n is an integer of 2 or more;
[formula 1-39]
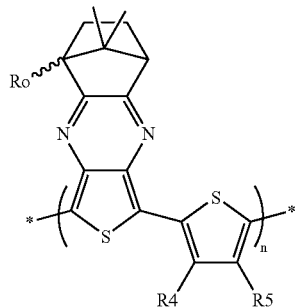

wherein n is an integer of 2 or more; and each of R4 and R5 is independently or simultaneously selected from the group consisting of H, an linear or branched aliphatic hydrocarbon having 1-20 carbon atoms, and an alkoxy group including a linear or branched aliphatic hydrocarbon having 1-20 carbon atoms; or R4 and R5 may form a fused ring together;

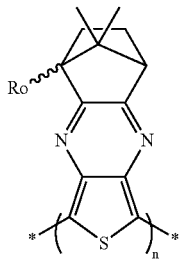

[formula 1-40]

wherein n is an integer of 2 or more;

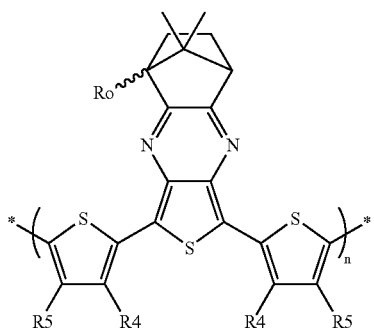

[formula 1-41]

wherein n is an integer of 2 or more; and each of R4 and R5 is independently or simultaneously selected from the group consisting of H, an linear or branched aliphatic hydrocarbon having 1-20 carbon atoms, and an alkoxy group including a linear or branched aliphatic hydrocarbon having 1-20 carbon atoms; or R4 and R5 may form a fused ring together.

3. The compound according to claim 1, wherein the compound represented by formula 1 is for use in an organic light emitting device as a light emitting material.

4. A method for preparing a compound of formula 1 according to claim 1, comprising the steps of:
(a) coupling a boronic acid having a substituent R1, a boronic acid having a substituent R2 and 2,5-dihalogen-3,4-dinitrothiophen in the presence of a base by adding a Pd-containing catalyst, wherein R1 and R2 are the same as defined in claim 1;
(b) reducing nitro ($NO_2$) groups in the compound obtained from step (a) into amino ($NH_2$) groups; and
(c) reacting the compound obtained from step (b) with camphorquinone.

5. A method for preparing a compound of formula 1 according to claim 1, comprising the steps of:
(a) introducing halogen atoms into 2,5-position of 3,4-diaminothiophen compound;
(b) reacting the compound obtained from step (a) with camphorquinone to form a thianopyrazine compound; and
(c) coupling a boronic acid having a substituent R1, a boronic acid having a substituent R2 and 2,5-dihalogen thianopyrazine compound obtained from step (b) in the presence of a base by adding a Pd-containing catalyst, wherein R1 and R2 are the same as defined in claim 1.

6. An organic light emitting device including a first electrode, an organic film having one or more layers and a second electrode, laminated successively, wherein at least one layer of the organic film includes at least a compound of formula 1 defined in claim 1.

7. The organic light emitting device according to claim 6, wherein the compound represented by formula 1 is present in at least one form selected from the group consisting of (R)-isomer, (S)-isomer and mixtures thereof.

8. The organic light emitting device according to claim 6, wherein the compound is selected from the group consisting of compounds represented by formulae 1-1 to 1-41:

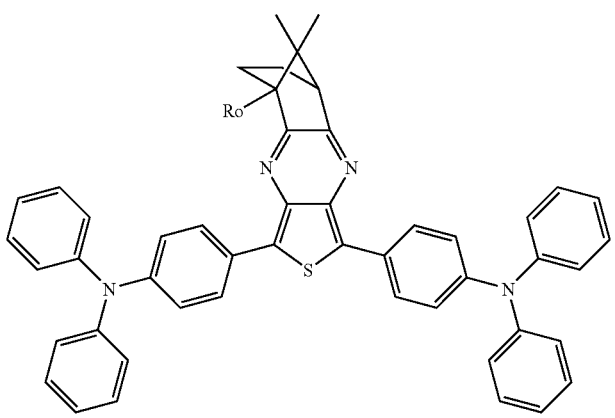

[formula 1-1]

[formula 1-2]
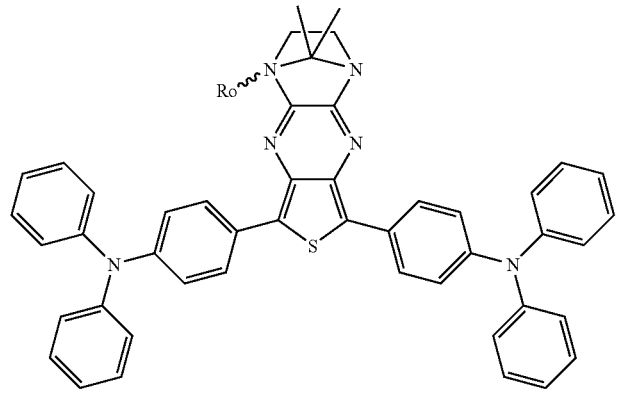
[formula 1-3]
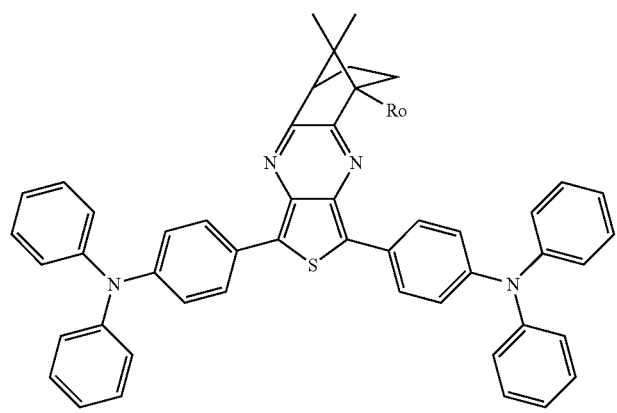
[formula 1-4]
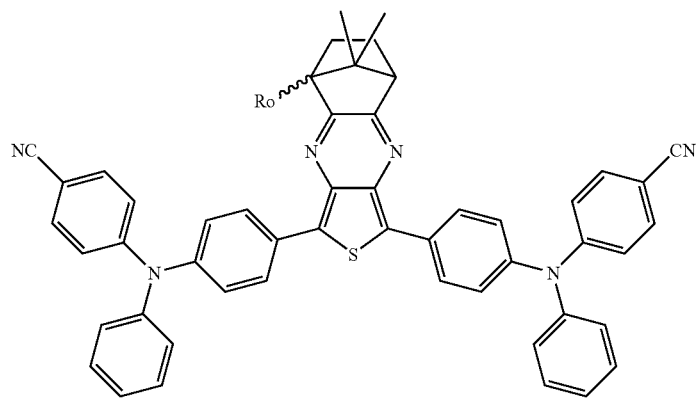
[formula 1-5]
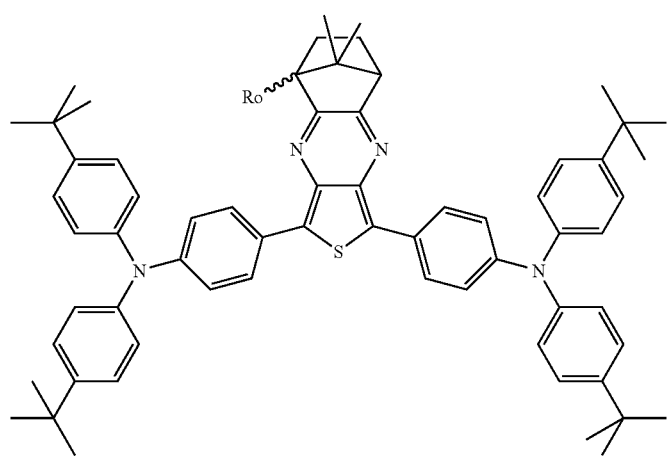

[formula 1-6]
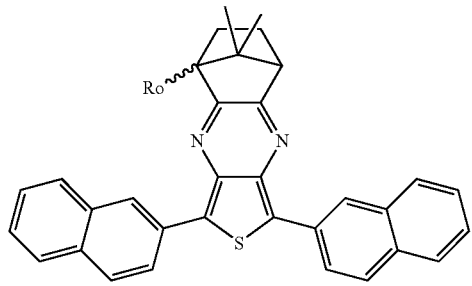
[formula 1-7]
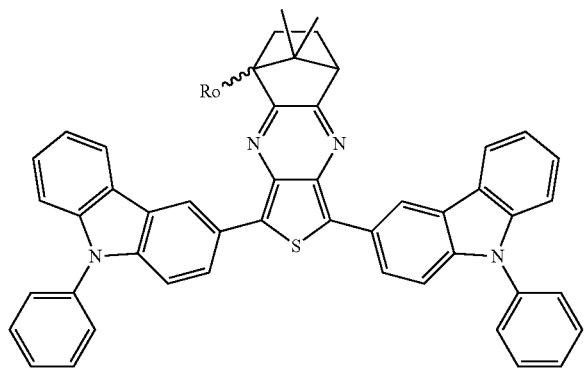
[formula 1-8]
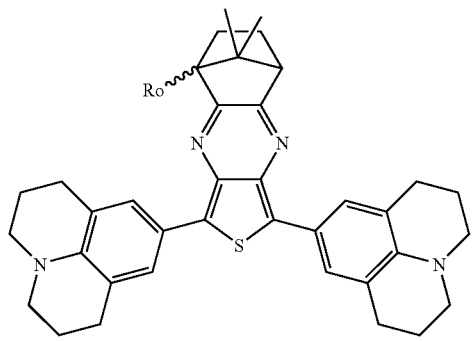
[formula 1-9]
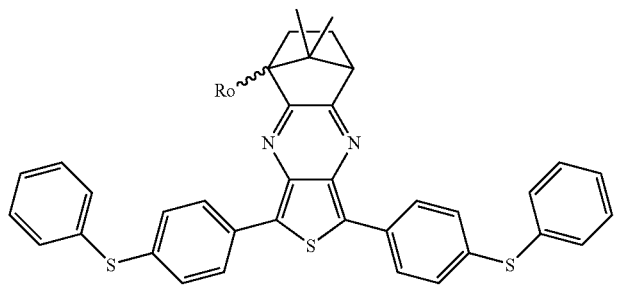
[formula 1-10]
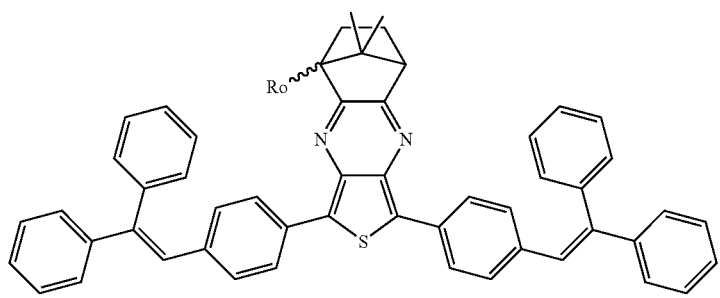

[formula 1-11]
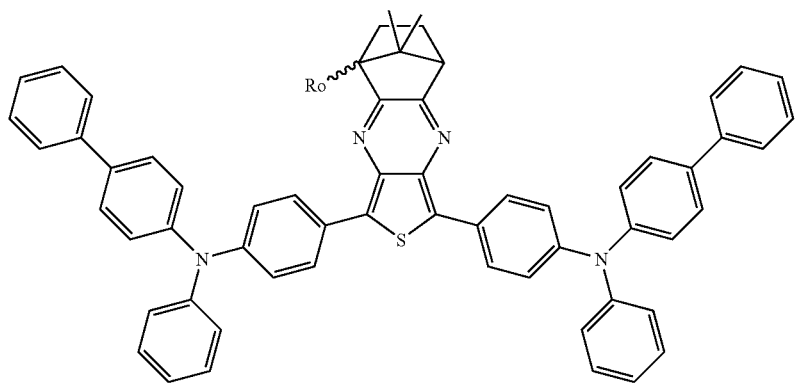
[formula 1-12]
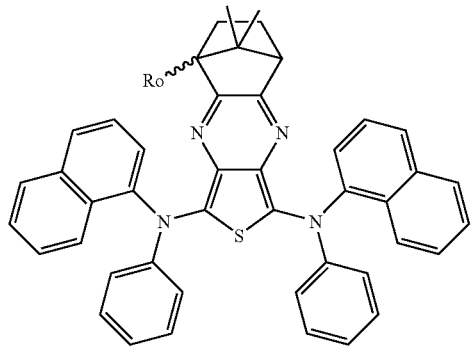
[formula 1-13]
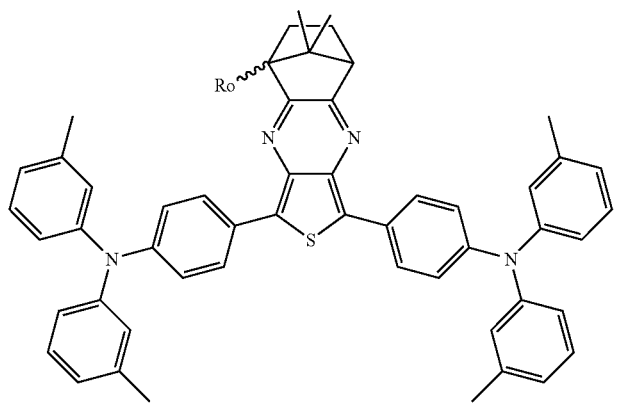
[formula 1-14]
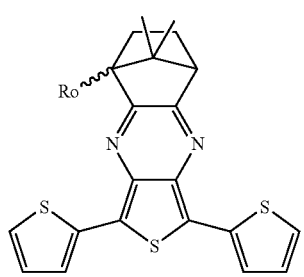

[formula 1-15]
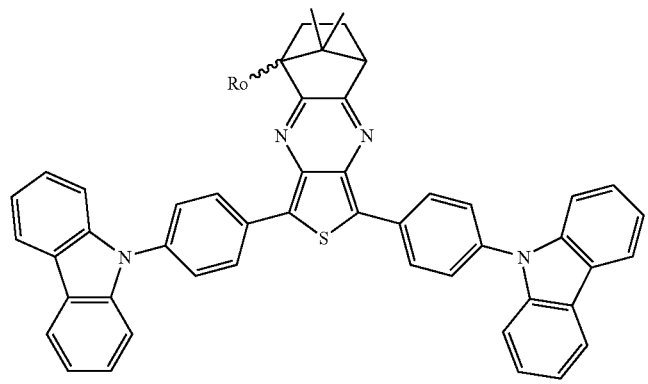
[formula 1-16]
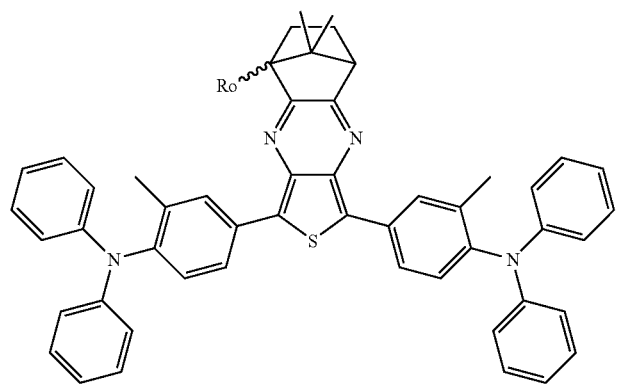
[formula 1-17]
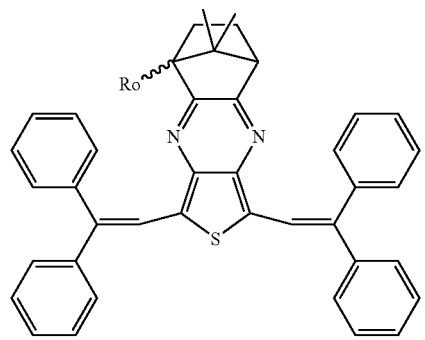
[formula 1-18]
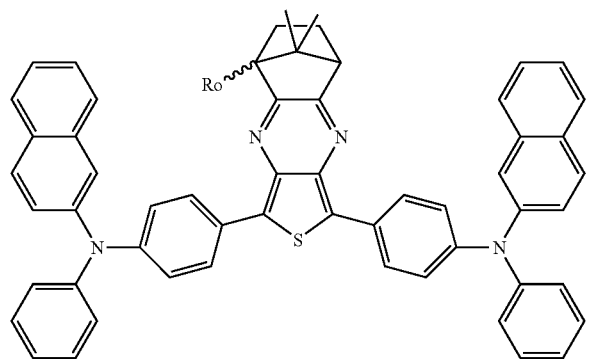

[formula 1-19]
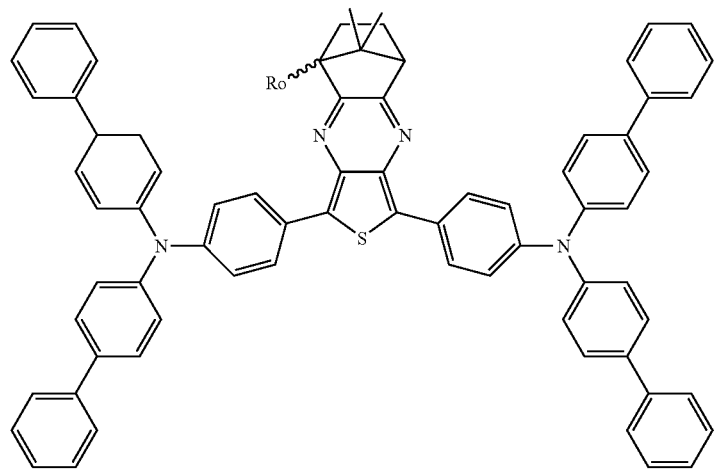
[formula 1-20]
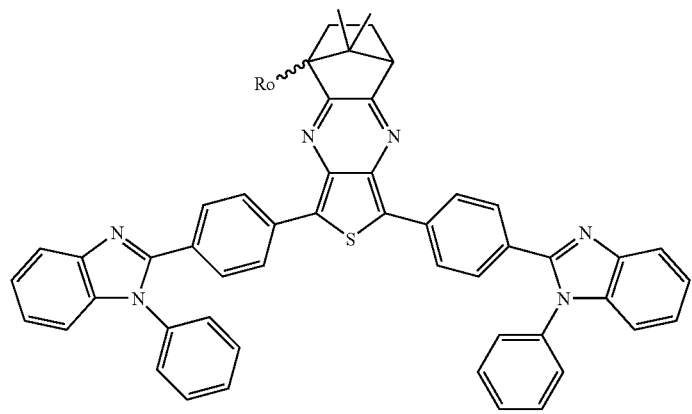
[formula 1-21]
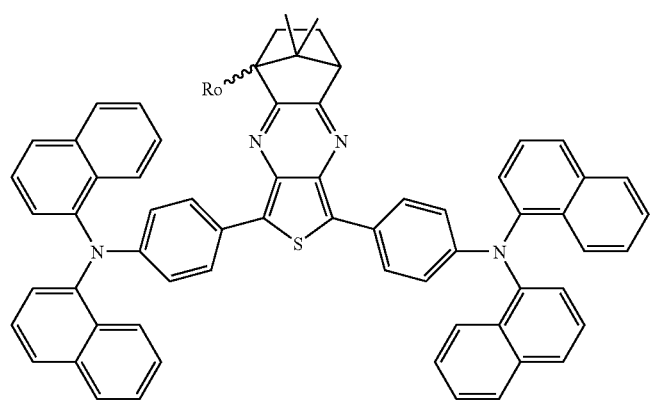
[formula 1-22]
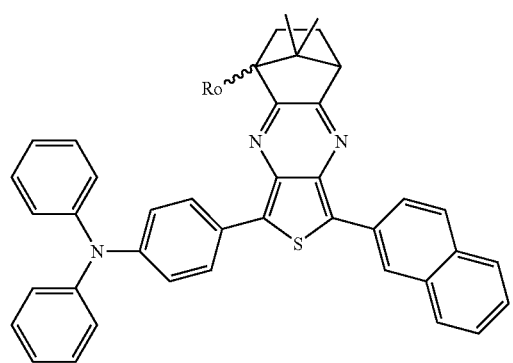

[formula 1-23]
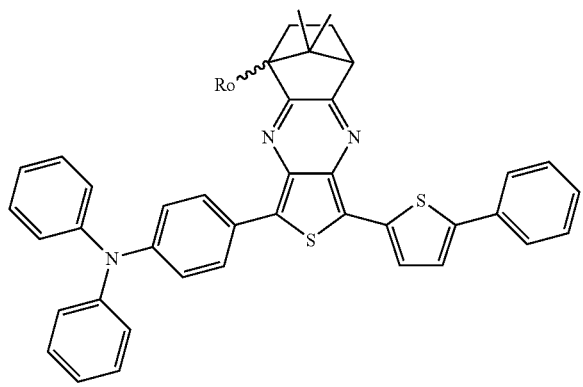
[formula 1-24]
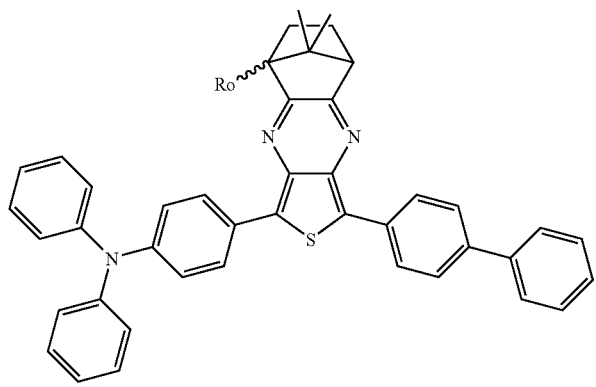
[formula 1-25]
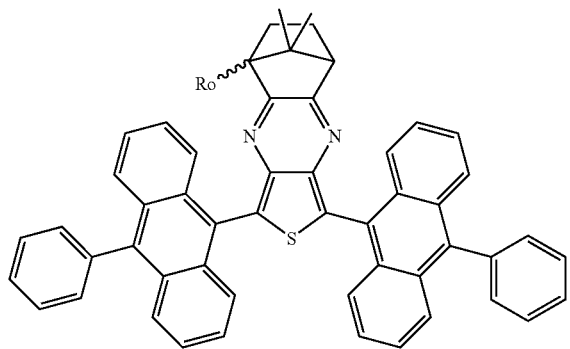
[formula 1-26]
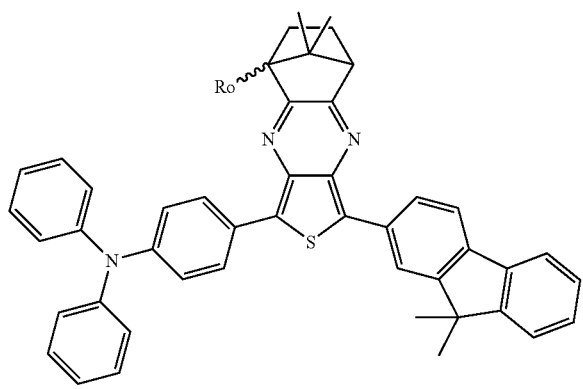

-continued
[formula 1-27]
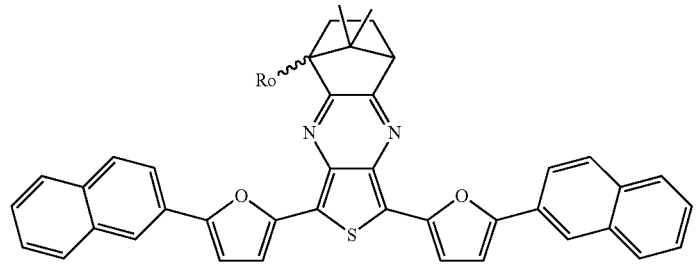
[formula 1-28]
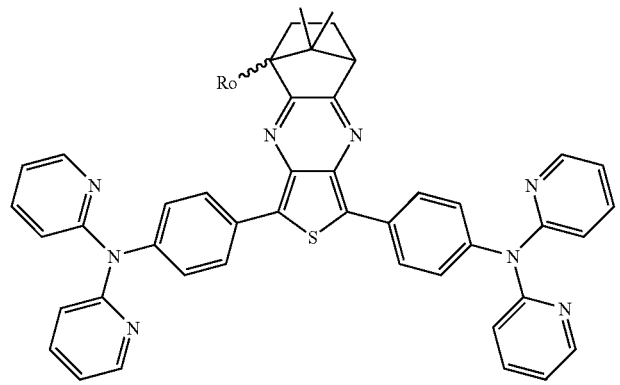
[formula 1-29]
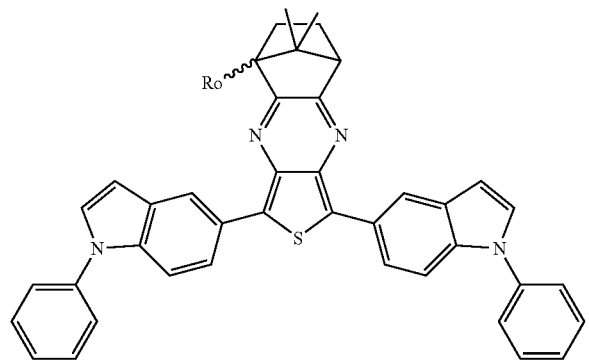
[formula 1-30]
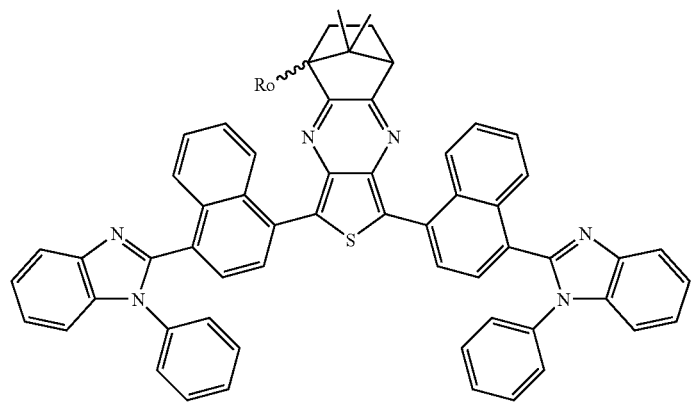

[formual 1-31]
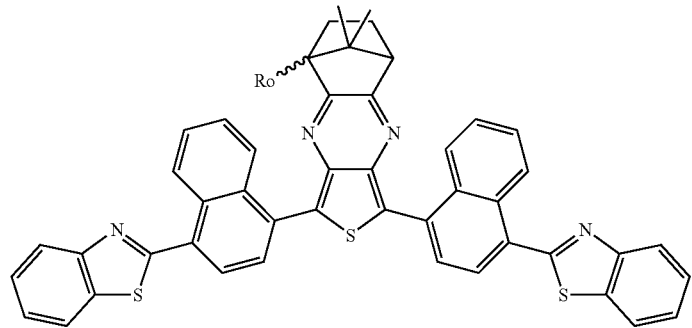
[formula 1-32]
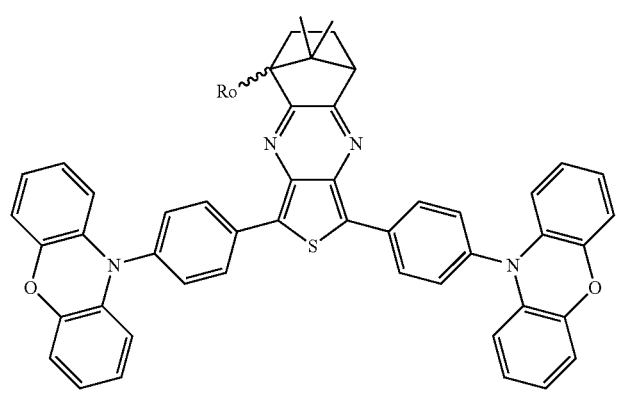
[formula 1-33]
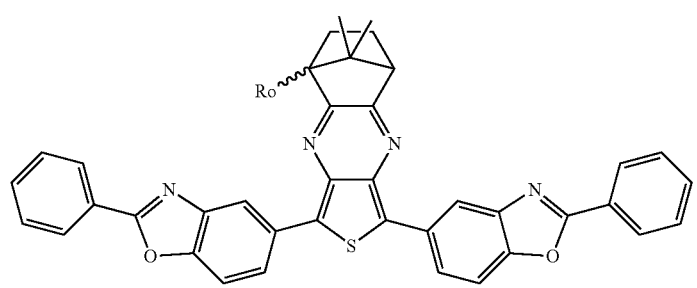
[formula 1-34]
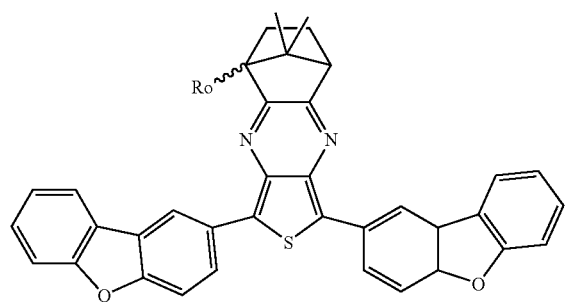

-continued
[formula 1-35]
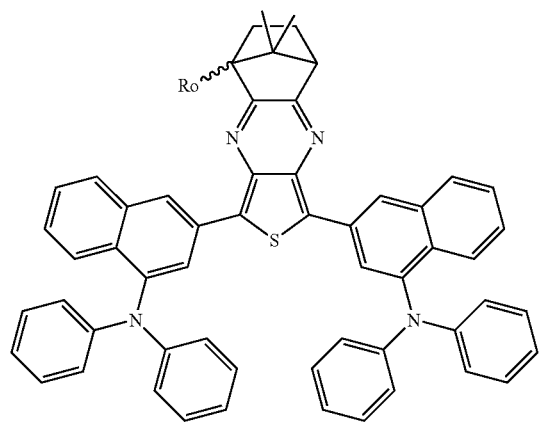
[formula 1-36]
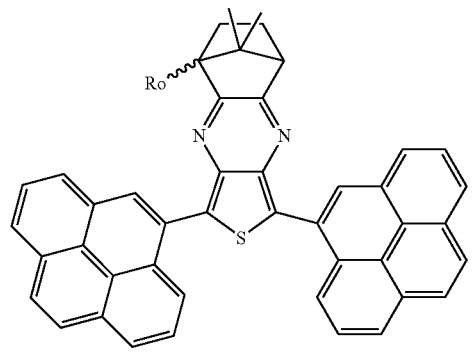
[formula 1-37]
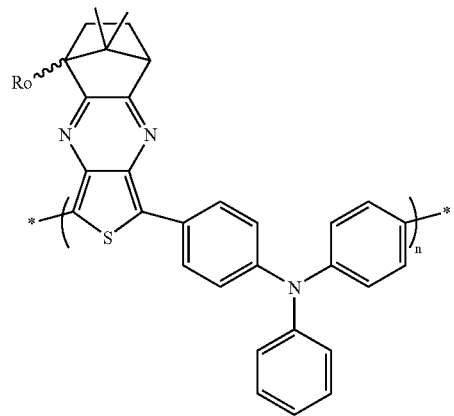
wherein n is an integer of 2 or more;

[formula 1-38]

wherein n is an integer of 2 or more;

[formula 1-39]

wherein n is an integer of 2 or more; and each of R4 and R5 is independently or simultaneously selected from the group consisting of H, an linear or branched aliphatic hydrocarbon having 1-20 carbon atoms, and an alkoxy group including a linear or branched aliphatic hydrocarbon having 1-20 carbon atoms; or R4 and R5 may form a fused ring together;

[formula 1-40]

wherein n is an integer of 2 or more;

[formula 1-41]

wherein n is an integer of 2 or more; and each of R4 and R5 is independently or simultaneously selected from the group consisting of H, an linear or branched aliphatic hydrocarbon having 1-20 carbon atoms, and an alkoxy group including a linear or branched aliphatic hydrocarbon having 1-20 carbon atoms; or R4 and R5 may form a fused ring together.

* * * * *